United States Patent [19]

Allen et al.

[11] Patent Number: 5,198,438
[45] Date of Patent: Mar. 30, 1993

[54] ANGIOTENSIN II ANTAGONISTS INCORPORATING A SUBSTITUTED THIOPHENE OR FURAN

[75] Inventors: Eric E. Allen, Somerset; Ralph A. Rivero, Tinton Falls; Nancy Kevin, Clifton, all of N.J.

[73] Assignee: Merck & Co., Inc., Rahway, N.J.

[21] Appl. No.: 846,156

[22] Filed: Mar. 11, 1992

Related U.S. Application Data

[63] Continuation of Ser. No. 696,666, May 7, 1991, abandoned.

[51] Int. Cl.[5] ............... C07D 405/10; C07D 405/14; C07D 409/10; C07D 409/14; A61K 31/415
[52] U.S. Cl. .................... 514/235.8; 514/63; 514/64; 514/382; 514/397; 514/445; 544/139; 548/110; 548/315.1; 548/252; 548/315.4; 549/4; 549/65
[58] Field of Search ............... 548/336, 252; 514/397, 514/235.8, 382; 544/139

[56] References Cited

U.S. PATENT DOCUMENTS 4,880,804  11/1989  Carini et al. ............ 514/234.5

FOREIGN PATENT DOCUMENTS

| | | |
|---|---|---|
| A58696/90 | 1/1991 | Australia . |
| 0253310 | 1/1988 | European Pat. Off. . |
| 0409332 | 1/1988 | European Pat. Off. . |
| 0260613 | 3/1988 | European Pat. Off. . |
| 0323841 | 7/1989 | European Pat. Off. . |
| 0324377 | 7/1989 | European Pat. Off. . |
| 0400974 | 5/1990 | European Pat. Off. . |
| 0392317 | 10/1990 | European Pat. Off. . |
| 0399731 | 11/1990 | European Pat. Off. . |
| 0399732 | 11/1990 | European Pat. Off. . |
| 0403158 | 12/1990 | European Pat. Off. . |
| 0403159 | 12/1990 | European Pat. Off. . |
| 0411766 | 2/1991 | European Pat. Off. . |
| 0412594 | 2/1991 | European Pat. Off. . |
| 0415886 | 3/1991 | European Pat. Off. . |
| 0419048 | 3/1991 | European Pat. Off. . |
| 0429257 | 5/1991 | European Pat. Off. . |
| 0430709 | 6/1991 | European Pat. Off. . |
| 0434249 | 6/1991 | European Pat. Off. . |
| 0468372 | 1/1992 | European Pat. Off. . |
| 0480204 | 4/1992 | European Pat. Off. . |
| 8911855 | 5/1989 | United Kingdom . |
| 9005843 | 3/1990 | United Kingdom . |

Primary Examiner—Mary C. Lee
Assistant Examiner—Lenora Ava Miltenberger
Attorney, Agent, or Firm—Valerie J. Camara; William H. Nicholson; Joseph F. DiPrima

[57] ABSTRACT

Substituted imidazoles attached through a methylene bridge to novel substituted phenyl thiophene or phenyl furan derivative of the Formula I are useful as angiotensin II antagonists.

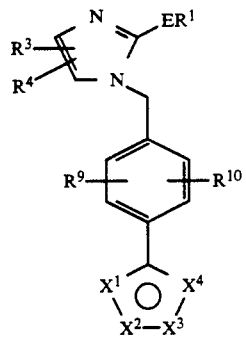

9 Claims, No Drawings

ANGIOTENSIN II ANTAGONISTS INCORPORATING A SUBSTITUTED THIOPHENE OR FURAN

The present application is a continuation in part of U.S. Ser. No. 07/696,666 filed May 7, 1991, now abandoned.

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens*, A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non peptide compounds have been described as A II antagonists. Illustrative of such compounds are those disclosed in U.S. Pat. Nos. 4,207,324; 4,340,598, 4,576,958; 4,582,847; and 4,880,804 and in European Patent Applications 028,834; 245,637; 253,310; and 291,969; and in articles by A. T. Chiu, et al. [*Eur. J. Pharm. Exp.* 157, 13–21 (1988)] and by P. C. Wong, et al. [*J Pharm. Exp. Therap*, 247, 1–7(1988). All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in any US Patent, European Applications or literature publication are of the type containing substituted imidazoles bonded through an alkyl bridge to a novel substituted phenyl thiophene or phenyl furan of the type disclosed herein. The quinazolin-4(1H)-ones, triazolinones, triazolinimines, and pyrimidinones have been disclosed in earlier U.S. Patent applications focusing on the heterocyclic fragment of the antagonist design. The Ser. Nos. of these applications are 351,508; 358,971; 375,655; 360,673; 375,217; and 386,328. Related applications disclose 6-membered ring fused imidazoles, (U.S. Ser. No. 675,371, filed Mar. 26, 1991) quinazolinones, triazolinones and pyrimidinones incorporating a thiophene or furan moiety.

BRIEF DESCRIPTION OF THE INVENTION

This invention is directed to substituted imidazoles attached through a methylene bridge to novel substituted phenylthiophene or phenylfuran derivative to give compounds of the Formula I, which are angiotensin II antagonists and are useful in the treatment of hypertension and congestive heart failure. The compounds of the invention are useful as ocular antihypertensives.

Specifically, the compounds of this invention contain an imidazole moiety which is substituted at the specified positions and to which a methylene bridge connecting a novel substituted phenyl thiophene or phenyl furan group as defined by the lower portion of Formula I, is attached. Additionally, pharmaceutically acceptable compositions of these novel compounds, as the sole therapeutically active ingredient and in combination with diuretics and other antihypertensive agents, including beta blockers, angiotensin converting enzyme inhibitors, calcium channel blockers or a combination thereof are disclosed and claimed. Further, methods of treating hypertension and congestive heart failure are described and claimed.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

DETAILED DESCRIPTION OF THE INVENTION

This invention relates to compounds of the general Formula I:

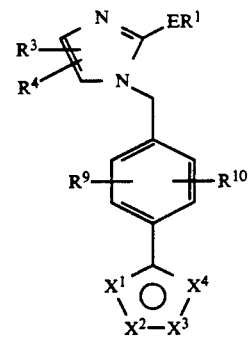

and its pharmaceutically acceptable salt wherein:
$R^1$ is:
(a) $(C_1-C_6)$-alkyl. $(C_2-C_6)$-alkenyl or $(C_2-C_6)$-alkynyl each of which is unsubstituted or substituted with a substituent selected from the group consisting of:
 i) aryl as defined below,
 ii) $(C_3-C_7)$-cycloalkyl, iii) Cl, Br, I, F,
iv) OH,
v) $NH_2$,
vi) $NH(C_1-C_4)$-alkyl,
vii) $N[(C_1-C_4 \text{ alkyl}]_2$,
viii) $NHSO_2R^2$,
ix) $CF_3$,
x) $COOR^2$, or
xi) $SO_2NHR^{2a}$;

(b) aryl, wherein aryl is defined as phenyl or naphthyl, unsubstituted or substituted with 1 or 2 substituents selected from the group consisting of:
  i) Br, I, Cl, F,
  ii) $(C_1-C_4)$-alkyl,
  iii) $(C_1-C_4)$-alkoxy,
  iv) $(C_3-C_7)$-cycloalkyl,
  v) $(C_3-C_{10})$-alkenyl,
  vi) $(C_1-C_4)$-alkylthio,
  vii) OH,
  viii) $CO_2H$,
  ix) $CO_2-(C_1-C_4)$-alkyl,
  x) $NO_2$,
  xi) $CF_3$,
  xii) $NH_2$,
  xiii) $NH[(C_1-C_4)$-alkyl],
  xiv) $N[(C_1-C_4)$-alkyl]$_2$, or
  xv) $SO_2NR^{2a}R^{2a}$, (c) heteroaryl, wherein heteroaryl is defined as a 5 or 6- membered heteroaromatic moiety, which can contain one or two members selected from the group consisting of N, O, S and wherein the heteroaryl is unsubstituted, monosubstituted or disubstituted with substituents selected from the group consisting of:
  i) Cl, Br, I, or F,
  ii) OH.
  iii) SH,
  iv) $NO_2$,
  v) $(C_1-C_4)$-alkyl,
  vi) $(C_2-C_4)$-alkenyl,
  vii) $(CC_2-C_4)$-alkynyl,
  ii) $(C_1-C_4)$-alkoxy,
  ix) $CF_3$,
  xii) $NH_2$,
  xiii) $NH[(C_1-C_4)$-alkyl],
  xiv) $N[(C_1-C_4)$-alkyl$]_2$,
  xv) $CO_2H$, or
  xvi) $CO_2-(C_1-C_4)$-alkyl, or (d) $(C_1-C_4)$-polyfluoroalkyl;

(a) a single bond,
(b) $-S(O)_n(CH_2)_s-$, or (c) $-O-$;

n is 0 to 2;
s is 0 to 5;
m is 1 to 5;
p is 0 to 3;
x is 1 to 10;

$R^3$ is:
(a) H,
(b) $(C_1-C_6)$-alkyl, $(C_2-C_6)$-alkenyl or $(C_2-C_6)$-alkynyl,
(c) Cl, Br, I. F,
(d) $NO_2$
(e) $CF_3$,
(f) $(C_1-C_8)$-polyfluoroalkyl,
(g) $C_6F_5$,
(h) CN,
(i) phenyl,
(j) phenyl-$(C_1-C_3)$-alkyl,
(k) phenyl and phenyl-$(C_1-C_3)$-alkyl substituted on the phenyl ring with one or two substituents selected from:
  i) $(C_1-C_4)$-alkyl,
  ii) $(C_1-C_4)$-alkoxyl,
  iii) F, Cl, Br, I,
  iv) hydroxyl,
  v) methoxyl,
  vi) $CF_3$,
  vii) $CO_2R^{2a}$,
  viii) $NO_2$, or
  ix) $SO_2NR^{2a}R^{2a}$;

$R^4$ is:
(a) H,
(b) CN,
(c) $(C_1-C_8)$-alkyl,
(d) $(C_3-C_6)$-alkenyl,
(e) $(C_1-C_8)$ polyfluoroalkyl,
(f) $(C_1-C_8)$-polyfluoroalkenyl,
(g) $CF_2CF_3$,
(h) $CO_2R^{2a}$,
(i) phenyl,
(j) phenyl-$(CC_2-C_6)$-alkenyl, (k) $-\overset{O}{\underset{\|}{C}}-R^5$, (l) $-(CH_2)_{x-1}-\overset{OR^6}{\underset{|}{CH}}-R^6$, (m) $-(CH_2)_x-O\overset{O}{\underset{\|}{C}}R^7$, (n) $-(CH_2)_x-S(O)_nR^8$, (o) $-CH=CH(CH_2)_s-O\overset{O}{\underset{\|}{C}}R^8$, (p) $-CH=CH(CH_2)_s\overset{O}{\underset{\|}{C}}R^6$, (q) $-(CH_2)_s-\overset{CH_3}{\underset{|}{CH}}-\overset{}{\underset{\underset{O}{\|}}{C}}R^8$, (r) $-(CH_2)_x-\overset{O}{\underset{\|}{C}}R^8$, (s) $-(CH_2)_x-O\overset{O}{\underset{\|}{C}}NHR^5$, (t) $-(CH_2)_x-O\overset{S}{\underset{\|}{C}}NHR^5$, (u) $(CH_2)_x-NHSO_2R^5$,
(v) $-(CH_2)_xF$,
(w) $-(CH_2)_m$-imidazol-1-yl,
(x) $-(CH_2)_m$-1,2,3-triazolyl, unsubstituted or substituted with one or two groups selected from:
  i) $CO_2CH_3$,
  ii) $(C_1-C_4)$-alkyl,
(y) tetrazol-5-yl,

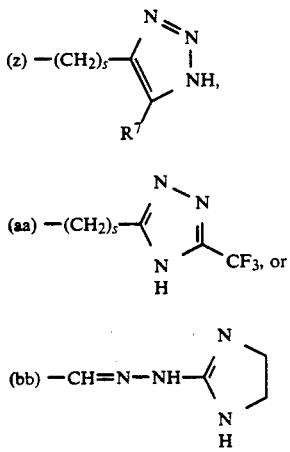

R² is:
 (a) H, or
 (b) (C₁-C₆)-alkyl;
R²ᵃ is:
 (a) R²,
 (b) CL₂-aryl, or
 (c) aryl;
R⁵ is:
 (a) (C₁-C₈)-alkyl,
 (b) (C₁-C₈)-polyfluoroalkyl,
 1 adamantyl,
 (d) 1-naphthyl,
 (e) (1-naphthyl)ethyl,
 (f) —(CH₂)ₚ-phenyl;
R⁶ is:
 (a) H,
 (b) (C₁-C₆)-alkyl,
 (c) (C₃-C₆)-cycloalkyl,
 (d) phenyl, or
 (e) benzyl;
R⁷ is:
 (a) H,
 (b) (C₁-C₈)-alkyl,
 (c) (C₁-C₈)-polyfluoroalkyl,
 (d) (C₃-C₆)-cycloalkyl,
 (e) phenyl, or
 (f) benzyl,
R⁸ is:
 (a) H,
 (b) (C₁-C₆)-alkyl,
 (c) (C₃-C₆)-cycloalkyl,
 (d) —(CH₂)ₚ-phenyl,
 (e) —OR⁶,
 (f) morpholin-4-yl,
 (g) —NR¹⁵R¹⁶;
R⁹ and R¹⁰ are each independently:
 (a) H,
 (b) Cl, Br, I, F,
 (c) NO₂,
 (d) (C₁-C₆)-alkyl,
 (e) (C₁-C₆)-acyloxy,
 (f) C₃-C₆)-cycloalkyl,
 (g) (C₁-C₆)-alkoxy,
 (h) —NHSO₂R²ᵃ,
 (i) hydroxy—(C₁-C₄)-alkyl,
 (j) (C₁-C₄)-alkyl-aryl,
 (k) S(O)ₙ—(C₁-C₄)-alkyl,
 (l) NR²ᵃR²ᵃ,
 (m) CF₃,
 (n) —SO₂NHR²ᵃ,
 (o) furyl,
 (p) aryl, or
 (q) when R⁹ and R¹⁰ are bonded to adjacent carbon atoms, they can be Joined to form a phenyl or naphthyl ring;
—X¹—X²—X³—X⁴— is:
 (a) -Y-CR¹¹-CR¹²CZ-,
 (b) -CR¹¹-Y-CR¹²-CZ-,
 (c) -CR¹¹-CR¹²-Y-CZ-,
 (d) -Y-CR¹¹- CZ-CR¹²-,
 (e) -CR¹¹-Y CZ-CR¹²-, or
 (f) -CR¹¹- CR¹²-CZ-Y-,
Y is: O, S, SO, or SO₂,
Z is:
 (a) —CO₂R²ᵃ
 (b) —SO₃R¹³, (c) —NHSO₂CF₃, (d) —PO(OR¹³)₂,
  (e) —SO₂NHR²ᵃ,
 (f) —CONHOR¹³,

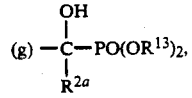

(h) —CN,
 (i) —SO₂NH-heteroaryl,
 (j) —CH₂SO₂NH-heteroaryl,
 (k) —SO₂NH—CO-R¹⁴,
 (l) —CH₂SO₂NH—CO R¹⁴,
 (m) CONH—SOZR¹⁴,
 (n) —CHZCONH—SOZR¹⁴,
 (o) —NHSOZNHCO-R¹⁴,
 (p) —NHCONHSOZ-R¹⁴,

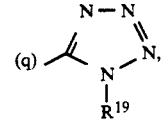

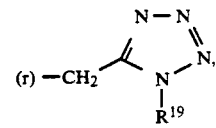

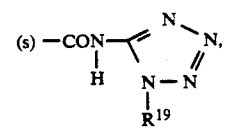

(t) —CONHNHSO₂CF₃,

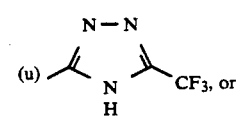

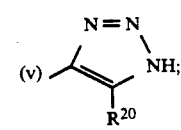

R¹¹ and R¹² are independently:

(a) H,
(b) Cl, Br, I, F,
(c) $NO_2$,
(d) $NH_2$,
(e) $NH[(C_1-C_4)\text{-alkyl}]$,
(f) $N[(C_1-C_4)\text{-alkyl}]_2$,
(g) $SO_2NHR^{2a}$,
(h) $CF_3$,
(i) $(C_1-C_7)$-alkyl,
(j) $(C_1-C_6)$-alkoxy,
(k) $(C_3-C_7)$-cycloalkyl,
(l) when $R^{11}$ and $R^{12}$ are bonded to adjacent carbon atoms, they can be Joined to form a phenyl or naphthyl ring,
(m) $O(CH_2)_{n+1}O(CH_2)_sCH_3$,
(n) $(CH_2)_{n+1}O(CH_2)_sCH_3$,
(o) $(CH_2)N(R^{2a})_2$,
(p) $(CH_2)_nN[CH_2CH_2]_2D$,
(q) $(CH_2)_nN[CH_2CH_2]_2CH_2$,
(r) $CH(OR^{2a})[(C_1-C_7)\text{-alkyl}]$,
(s) CHO,
(t) $CO_2R^{2a}$,
(u) $CH=CH-R^{2a}$,
(v) $CH_2CR^{2a}=C(R^{2a})_2$,
(w) $(CH_2)_nNCOR^{2a}$,
(x) $(C_1-C_4)$-alkyl-aryl, or
(y) $CH(R^{2a})_2$;

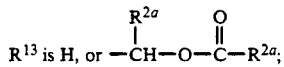

$R^{13}$ is H, or $-CH-O-C-R^{2a}$;

$R^{14}$ is
(a) aryl,
(b) heteroaryl,
(c) $(C_3-C_7)$-cycloalkyl,
(d) $(C_1-C_7)$-alkyl, unsubstituted or substituted with a substituent selected from the group consisting of: aryl, heteroaryl, -OH, -SH, $(C_1-C_4)$-alkyl, $(C_1-C_4)$-alkoxy, $-S(C_1-C_4)$-alkyl, $-CF_3$, Cl, Br, F, I, $-NO_2$, $-CO_2H$, $CO_2-(C_1-C_4)$-alkyl, $-NH_2$, $-N[(C_1-C_4)\text{-alkyl}]_2$, $-PO_3H$ or $PO(OH)(O-(C_1-C_4)\text{-alkyl})$,
(e) $(C_1-C_7)$-alkoxy,
(f) $O(CH_2)_{n+1}O(CH_2)_sCH_3$,
(g) $(CH_2)_{n+1}O(CH_2)_sCH_3$,
(h) $CH(R^{2a})_2$,
(i) $(C_1-C_6)$-polyfluoroalkyl, or
(j) $-NH-(C_1-C_6)$-alkyl;

$R^{15}$ and $R^{16}$ are independently:
(a) H,
(b) $(C_1-C_4)$-alkyl,
(c) phenyl,
(d) benzyl, or
(e) α-methylbenzyl;

$R^{19}$ is:
(a) H,
(b) $(C_1-C_6)$-alkyl,
(c) $(C_2-C_4)$-alkenyl,
(d) $(C_1-C_4)$-alkoxy, or
(e) benzyl, wherein the phenyl is unsubstituted substituted with a substituent selected from the group consisting of: $-NO_2$, $-NH_2$, $-OH$ or $-OCH_3$; and $R^{20}$ is $-CN$, $-NO_2$, $-CO_2R^{2a}$, or $-CF_3$.

One embodiment of the novel compounds of the invention is that wherein:
$R^1$ is:
(a) $(C_1-C_6)$-alkyl, $(C_2-C_6)$-alkenyl or $(C_2-C_6)$-alkynyl each of which is unsubstituted or substituted with a substituent selected from the group consisting of:
i)-aryl, wherein aryl is defined as phenyl or naphthyl, unsubstituted or substituted with 1 or 2 substituents selected from the group consisting of:
i) Br, I, Cl, F,
ii) $(C_1-C_4)$-alkyl,
iii) $(C_1-C_4)$-alkoxy,
iv) $(C_3-C_7)$-cycloalkyl,
v) $(C_3-C_{10})$-alkenyl,
vi) $(C_1-C_4)$-alkylthio,
viii) $CO_2H$,
ix) $CO_2-(C_1-C_4)$-alkyl,
x) $NO_2$.
xi) $CF_3$,
xii) $NH_2$,
xiii) $NH[(C_1-C_4)\text{-alkyl}]$,
xiv) $N[(C_1-C_4)\text{-alkyl}]_2$,
xv) $SO_2NR^{2a}R^{2a}$,
ii) $C_3-C_7$-cycloalkyl,
iii) Cl, Br, I, F,
iv) OH,
vi) $NH(C_1-C_4)$-alkyl,
vii) $N[(C_1-C_4)\text{-alkyl}]_2$,
viii) $NHSO_2R^2$,
ix) $CF_3$,
x) $COOR^2$, or
xi) $SO_2NHR^{2a}$, or
(b) $(C_1-C_4)$-polyfluoroalkyl;

E is a single bond, or $-S-$;

$R^2$ is:
(a) H, or
(b) $(C_1-C_6)$-alkyl;

$R^{2a}$ is:
(a) $R^2$,
(b) $CH_2$-aryl, or
(c) aryl;

n is 0 to 2;
s is 0 to 5;
m is 1 to 5;
p is 0 to 3;
x is 1 to 10;

$R^3$ is:
(a) H,
(b) $(C_1-C_6)$-alkyl, $(C_2-C_6)$-alkenyl or $(C_2-C_6)$-alkynyl,
(c) Cl, Br, I, F,
(d) $NO_2$
(e) $CF_3$,
(f) $(C_1-C_8)$-polyfluoroalkyl,
(g) $C_6F_5$,
(h) CN,
(i) phenyl,
(j) phenyl-$(C_1-C_3)$-alkyl,
(k) phenyl and phenyl-$(C_1-C_3)$-alkyl substituted on the phenyl ring with one or two substituents selected from:
i) $(C_1-C_4)$-alkyl,
ii) $(C_1-C_4)$-alkoxyl,
iii) F, Cl, Br, I,
iv) hydroxyl,
v) methoxyl,
vi) $CF_3$,
vii) $CO_2R^{2a}$, viii) NO$_2$, or
ix) SO$_2$NR$^{2a}$R$^{2a}$;

R$^4$ is:
(a) H,
(b) CN,
(c) (C$_1$-C$_8$)-alkyl,
(d) (C$_3$-C$_6$)-alkenyl,
(e) (C$_1$-C$_8$)-polyfluoroalkyl,
(f) (C$_1$-C$_8$)-polyfluoroalkenyl,
(g) CF$_2$CF$_3$,
(h) CO$_2$R$^{2a}$,
(i) phenyl,
(j) phenyl-(C$_2$-C$_6$)-alkenyl, (k) 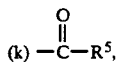

(l) 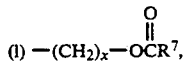

(m) —(CH$_2$)$_x$—X(O)$_2$R$^8$,
(n) —(CH$_2$)$_m$-1,2,3-triazolyl, unsubstituted or substituted with one or two groups selected from:
  i) CO$_2$CH$_3$,
  ii) (C$_1$-C$_4$)-alkyl,
(o) tetrazol-5-yl, or (p) 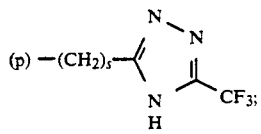

R$^5$ is:
(a) (C$_1$-C$_8$)-alkyl,
(b) (C$_1$-C$_8$)-polyfluoroalkyl,
(c) 1-adamantyl,
(d) 1-naphthyl,
(e) (1-naphthyl)ethyl, or
(f) —(CH$_2$)$_p$-phenyl;

R$^5$ is:
(a) H,
(b) (C$_1$-C$_6$)-alkyl,
(c) (C$_3$-C$_6$)-cycloalkyl,
(d) phenyl, or
(e) benzyl;

R$^7$ is:
(a) H,
(b) (C$_1$-C$_8$)-alkyl,
(c) (C$_1$-C$_8$)-polyfluoroalkyl,
(d) (C$_3$-C$_6$)-cycloalkyl,
(e) phenyl,
(f) benzyl;

R$^8$ is:
(a) H,
(b) (C$_1$-C$_6$)-alkyl,
(c) (C$_3$-C$_6$)-cycloalkyl,
(d) —(CH$_2$)$_p$-phenyl,
(e) OR$^6$,
(f) morpholin-4-yl,
(g) NR$^{15}$R$^{16}$;

R$^9$ and R$^{10}$ are each independently:
(a) H,
(b) Cl, Br, I, F,
(c) NO$_2$,
(d) (C$_1$-C$_6$)-alkyl,
(e) (C$_1$-C$_6$)-acyloxy,
(f) (C$_3$-C$_6$)-cycloalkyl,
(g) (C$_1$-C$_6$)-alkoxy,
(h) —NHSO$_2$R$^{2a}$,
(i) hydroxy-(C$_1$-C$_4$)-alkyl,
(j) (C$_1$-C$_4$)-alkyl-aryl,
(k) S(O)$_n$-(C$_1$-C$_4$)-alkyl,
(l) NR$^{2a}$R$^{2a}$,
(m) CF$_3$.
(n) —SO$_2$NHR$^{2a}$,
(o) furyl,
(p) aryl, or
(q) when R$^9$ and R$^{10}$ are bonded to adjacent carbon atoms, they can be Joined to form a phenyl or naphthyl ring;

—X$^1$—X$^2$—X$^3$—X$^4$— is:
(a) -Y—CR$^{11}$-CR$^{12}$-CZ-,
(b) -CR$^{11}$-Y-CR$^{12}$-CZ-,
(c) -CR$^{11}$-CR$^{12}$-Y-CZ-,
(d) -Y-CR$^{11}$-CZ-CR$^{12}$-,
(e) —CR$^{11}$-Y-CZ—CR$^{12}$, or
(f) CR$^{11}$—CR$^{12}$-CZ-Y-;

Y is: O, S, SO, or SO$_2$,
Z is:
(a) —CO$_2$R$^{2a}$,
(b) —NHSO$_2$CF$_3$,
(c) —SO$_2$NHR$^{2a}$,
(d) —CN,
(e) —SO$_2$NH-heteroaryl, wherein heteroaryl is an unsubstituted, monosubstituted or disubstituted five or six membered aromatic ring which can contain from 1 to 3 heteroatoms selected from the group consisting of O, N or S and wherein the substituents are members selected from the group consisting of: —OH, —SH, —(C$_1$-C$_4$)-alkyl, —(C$_1$-C$_4$)-alkoxy, —CF$_3$, Cl, Br, F, I, —NO$_2$, —CO$_2$H, —CO$_2$—(C$_1$-C$_4$)-alkyl, —NH$_2$, NH[(C$_1$-C$_4$)-alkyl]and —N[(C$_1$-C$_4$)-alkyl]$_2$,
(f) —SO$_2$NHCOR$^{14}$,
(g) —1H-tetrazol-5-yl,
(h) —CONH-1H-tetrazol-5-yl, or
(i) —CH$_2$-1H-tetrazol-5 yl;

R$^{11}$ and R$^{12}$ are independently:
(a) H,
(b) Cl, Br, I, F,
(c) NO$_2$,
(d) NH$_2$,
(e) NH[(C$_1$-C$_4$)-alkyl],
(f) N[(C$_1$-C$_4$)-alkyl]$_2$,
(g) SO$_2$NHR$^{2a}$,
(h) CF$_3$,
(i) (C$_1$-C$_4$)-alkyl,
(j) (C$_1$-C$_4$)-alkoxy,
(k) (C$_3$-C$_7$)-cycloalkyl,
(l) when R$^{11}$ and R$^{12}$ are bonded to adjacent carbon atom can be joined to form a phenyl or naphthyl ring,
(m) O(CH$_2$)$_{n+1}$O(CH$_2$)$_s$CH$_3$,
(n) (CH$_2$)$_{n+1}$O(CH$_2$)$_s$CH$_3$,
(o) (CH$_2$)N(R$^{2a}$)$_2$,
(p) (CH$_2$)$_n$N[CH$_2$CH$_2$]$_2$.X.
(q) (CH$_2$)$_n$N[CH$_2$CH$_2$]$_2$CH$_2$,
(r) CH(OR$^{2a}$)[(C$_1$-C$_7$)-alkyl],
(s) CHO,
(t) CO$_2$R$^{2a}$,
(u) CH=CH R$^{2a}$,
(v) CH$_2$CR$^{2a}$=C(R$^{2a}$)$_2$, (w) $(CH_2)_nNCOR^{2a}$,
(x) $(C_1-C_4)$-alkyl-aryl, or
(y) $CH(R^{2a})_2$;

$R^{13}$ is H, or $CH(R^4)$ O—$C(O)R^4$;

$R^{14}$ is
(a) -aryl,
(b) heteroaryl,
(c) $(C_3-C_7)$-cycloalkyl,
(d) $(C_1-C_7)$-alkyl, unsubstituted or substituted with a substituent selected from the group consisting of: aryl, heteroaryl, OH, -SH, $(C_1-C_4)$-alkyl, —$(C_1-C_6)$-alkoxy, —$S(C_1-C_6)$-alkyl, $(C_3-C_7)$-cycloalkyl, —$CF_3$, Cl, Br, F, I, -$NO_2$, —$CO_2H$, $CO_2$—$(C_1-C_4)$-alkyl, —$NH_2$, -N[$(C_1-C_4)$-alkyl]$_2$, —$PO_3H$ or $PO(OH)(O$—$(C_1-C_4)$-alkyl),
(e) $(C_1-C_7)$-alkoxy,
(f) $O(CH_2)_{n+1}O(CH_2)_sCH_3$,
(g) $(CH_2)_{n+1}O(CH_2)_sCH_3$,
(h) $CH(R^{2a})_2$,
(i) $(C_1-C_6)$-polyfluoroalkyl, or
(j) —NH $(C_1-C_6)$-alkyl;

$R^{15}$ and $R^{16}$ are independently:
(a) H,
(b) $(C_1-C_4)$-alkyl,
(c) phenyl,
(d) benzyl,
(e) α-methylbenzyl.

One embodiment of the invention is a compound of structural formula:

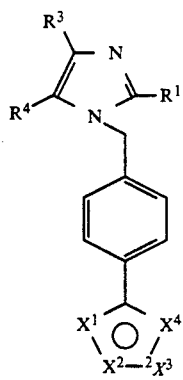

I or its pharmaceutically acceptable salt wherein:
$R^1$ is $(C_1-C_6)$-alkyl, $(C_3-C_8)$-cycloalkyl, or $(C_1-C_4)$-alkyl-$(C_3-C_8)$-cycloalkyl;
n is: 0, 1 or 2;
s is: 0 to 5;
$R^2$ is: H or $(C_1-C_6)$-alkyl;
$R^3$ is H, Cl, $(C_1-C_4)$-polyfluoroalkyl, $(C_1-C_4)$-alkylamino, $(C_1-C_4)$-acylamino;
$R^4$ is $CO_2H$, $CH_2OH$, or $CO_2(C_1-C_4)$-alkyl;
—$X^1$—$X^2$—$X^3$—$X^4$— is:
(a) Y-$CR^{11}$- $CR^{12}$-CZ ,
(b) —$CR^{11}$-Y-$CR^{12}$-CZ , or
(c) —$CR^{11}$—$CR^{12}$-Y-CZ-;

$R^{11}$ and $R^{12}$ are independently:
H, $C_1-C_6$-alkyl, $C_1-C_6$-alkoxy, $(C_1$—$C_4)$-alkyl-aryl, $O(CH_2)_{n+1}O(CH_2)_sCH_3$, $(CH_2)_{n+1}O(CH_2)_sCH_3$, $(CH_2)_nN[CH_2CH_2]_2O$ or when $R^{11}$ and $R^{12}$ are bonded to adjacent carbon atoms, they can joined to form an phenyl ring;
Y is: O, or S;
(a) $CO_2R^2$,
(b) 1H tetrazol-5-yl,
(c) $CONHSO_2R^{14}$,
(d) $SO_2NHR^{14}$,
(e) $NHSO_2R^{14}$,
(f) $SO_2NHCOR^{14}$, or
(g) $NHSO_2CF_3$, and $R^{14}$ is:
(a) $(C_1-C_6)$-alkyl,
(b) $(C_1-C_6)$-alkoxy,
(c) phenyl,
(d) $CH_2$phenyl,
(e) $CH(phenyl)_2$,

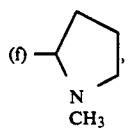

(g) $(C_3$—$C_6)$-cycloalkyl,
(h) $(C_1-C_3)$-alkyl—$(C_3-C_6)$-cycloalkyl,
(i) $(CH_2)_5NH_2$,
(j) $O(CH_2)_{n+1}O(CH_2)_sCH_3$,
(k) $(CH_2)_{n+1}O(CH_2)_sCH_3$,
(l) $(C_1-C_4)$-polyfluoroalkyl, or
(m) $NH(C_1-C_6)$-alkyl.

A subclass of this embodiment is a compound in which the structural formula is:

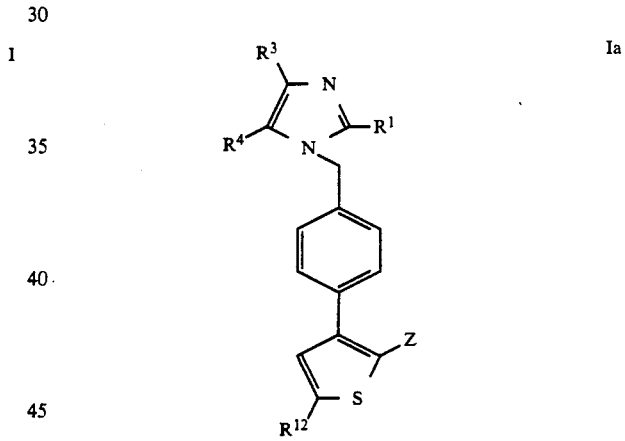

Ia or its pharmaceutically acceptable salt wherein:
$R^1$ is: ethyl, n-propyl, n-butyl, or cyclopropyl;
n is: 0, 1 or 2;
s is: 0 to 5;
$R^2$ is: H or $(C_1-C_6)$-alkyl;
$R^3$ is H, Cl, $(C_1-C_4)$-polyfluoroalkyl, $(C_1-C_4)$-alkylamino, $(C_1-C_4)$-acylamino;
$R^4$ is $CO_2H$, $CH_2OH$, or $CO_2(C_1-C_4)$-alkyl;
$R^{12}$ is: H, $(C_1-C_6)$-alkyl, $(C_1-C_6)$-alkoxy, -$CH_2$-phenyl, $O(CH_2)_{n+1}O(CH_2)_sCH_3$, $(CH_2)_{n+1}O(CH_2)_sCH_3$, or $CH_2N[CH_2CH_2]_2O$;
Z is:
(a) $CO_2R^2$,
(b) 1H-tetrazol-5-yl,
(c) $CONHSO_2R^{14}$,
(d) $SO_2NHR^{14}$,
(e) $NHSO_2R^{14}$,
(f) $SO_2NHCOR^{14}$, or
(g) $NHSO_2CF_3$; and $R^{14}$ is:
(a) $(C_1-C_6)$-alkyl, (b) (C$_1$-C$_6$)-alkoxy,
(c) phenyl,
(d) CH$_2$phenyl,
(e) CH(phenyl)$_2$, (f) 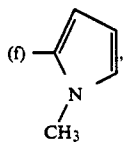

(g) (C$_3$-C$_6$)-cycloalkyl,
(C$_1$-C$_3$)-alkyl-(C$_3$-C$_6$)-cycloalkyl,
(i) (CH$_2$)$_5$NH$_2$,
(j) O(CH$_2$)$_{n+1}$O(CH$_2$)$_s$CH$_3$,
(k) (CH$_2$)$_{n+1}$O(CH$_2$)$_s$CH$_3$,
(l) (C$_1$-C$_4$)-polyfluoroalkyl, or
(m) NH-(C$_1$-C$_6$)-alkyl.

The compounds shown in the table below are representative of an embodiment of the invention:

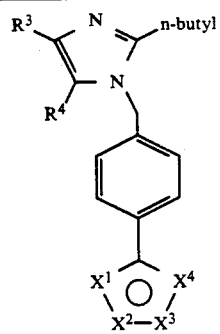

| R$^3$ | R$^4$ | —X$^1$—X$^2$—X$^3$—X$^4$— | R$^{12}$ | Z |
|---|---|---|---|---|
| Cl | CH$_2$OH | —C—C—S—CZ— (fused benzene) | | SO$_2$NHCOPh |
| Cl | CO$_2$H | —C—C—S—CZ— (fused benzene) | | SO$_2$NHCOPh |
| Cl | CH$_2$OH | —CH—CH—S—CZ— | | SO$_2$NHCOPh |
| Cl | CO$_2$H | —CH—CH—S—CZ— | | SO$_2$NHCOPh |
| CF$_3$ | CO$_2$H | —CH—CH—S—CZ— | | 1H-tetrazol-5-yl |
| CF$_2$CF$_3$ | CO$_2$H | —CH—CH—S—CZ— | | 1H-tetrazol-5-yl |
| Cl | CO$_2$H | —CH—CH—O—CZ— | | 1H-tetrazol-5-yl |
| Cl | CH$_2$OH | —CH—CH—O—CZ— | | 1H-tetrazol-5-yl |
| Cl | CO$_2$H | —C—C—S—CZ— (fused benzene) | | 1H-tetrazol-5-yl |
| Cl | CH$_2$OH | —C—C—S—CZ— (fused benzene) | | 1H-tetrazol-5-yl |
| NO$_2$ | CO$_2$H | —CH—CH—S—CZ— | | SO$_2$NHCOPh |
| CF$_3$ | CO$_2$H | —CH—CH—S—CZ— | | SO$_2$NHCOPh |
| Cl | CH$_2$OH | —CH—CH—S—CZ— | | 1H-tetrazol-5-yl |
| Cl | CH$_2$OH | —CH—CR$^{12}$—S—CZ— | Me | SO$_2$NHCOPh |
| Cl | CH$_2$OH | —CH—CR$^{12}$—S—CZ— | Et | SO$_2$NHCOPh |
| Cl | CH$_2$OH | —CH—CR$^{12}$—S—CZ— | nPr | SO$_2$NHCOPh |
| Cl | CH$_2$OH | —CH—CR$^{12}$—S—CZ— | nBu | SO$_2$NHCOPh |
| Cl | CH$_2$OH | —CH—CR$^{12}$—S—CZ— | iBu | SO$_2$NHCOPh |
| Cl | CH$_2$OH | —CH—CR$^{12}$—S—CZ— | nPn | SO$_2$NHCOPh |
| Cl | CH$_2$OH | —CH—CR$^{12}$—S—CZ— | Bn | SO$_2$NHCOPh |
| Cl | CH$_2$OH | —CH—CR$^{12}$—S—CZ— | CH$_2$N(CH$_2$CH$_2$)$_2$O | SO$_2$NHCOPh |
| Cl | CH$_2$OH | —CH—CR$^{12}$—S—CZ— | CH$_2$N(CH$_2$CH$_2$)$_2$O | SO$_2$NHCOCH(Ph)$_2$ |
| Cl | CH$_2$OH | —CH—CR$^{12}$—S—CZ— | nPr | SO$_2$NHCO(CH$_2$)$_2$OMe |
| Cl | CH$_2$OH | —CH—CR$^{12}$—S—CZ— | Me | SO$_2$NHCOCH$_2$Ph |
| Cl | CH$_2$OH | —CH—CR$^{12}$—S—CZ— | Me | SO$_2$NHCOCH(Ph)$_2$ |
| Cl | CH$_2$OH | —CH—CR$^{12}$—S—CZ— | Et | SO$_2$NHCOCH(Ph)$_2$ |
| Cl | CH$_2$OH | —CH—CR$^{12}$—S—CZ— | Et | SO$_2$NHCOCH$_2$OEt |
| Cl | CH$_2$OH | —CH—CR$^{12}$—S—CZ— | nBu | SO$_2$NHCOCH$_2$OEt |
| Cl | CH$_2$OH | —CH—CR$^{12}$—S—CZ— | nPr | SO$_2$NHCOCH$_2$OBu |

| | | | | |
|---|---|---|---|---|
| Cl | CH₂OH | —CH—CR¹²—S—CZ— | nBu | SO₂NHCO(CH₂)₂-cyclopentyl |
| Cl | CH₂OH | —CH—CR¹²—S—CZ— | iBu | SO₂NHCOCH₂OBu |
| Cl | CH₂OH | —CH—CR¹²—S—CZ— | iBu | SO₂NHCOCH₂OEt |
| Cl | CH₂OH | —CH—CR¹²—S—CZ— | nPn | SO₂NHCOCH₂OEt |
| Cl | CH₂OH | —CH—CR¹²—S—CZ— | nPn | SO₂NHCOCH₂OBu |
| Cl | CH₂OH | —CH—CR¹²—S—CZ— | nPn | SO₂NHCO₂—N-methylpyrrole |
| Cl | CH₂OH | —CH—CR¹²—S—CZ— | nPr | SO₂NHCO₂—N-methylpyrrole |
| Cl | CH₂OH | —CH—CR¹²—S—CZ— | nPr | SO₂NHCOOCH₂CH(Me)₂ |
| Cl | CH₂OH | —CH—CR¹²—S—CZ— | iBu | SO₂NHCOO(CH₂)₂OMe |
| Cl | CH₂OH | —CH—CR¹²—S—CZ— | nBu | SO₂NHCO(CH₂)₅NHCO₂-t-butyl |
| Cl | CH₂OH | —CH—CR¹²—S—CZ— | nBu | SO₂NHCO(CH₂)₅NH₂ |
| Cl | CH₂OH | —CH—CR¹²—S—CZ— | iBu | SO₂NHCO(CH₂)₅NHCO₂-t-butyl |
| Cl | CH₂OH | —CH—CR¹²—S—CZ— | iBu | SO₂NHCO(CH₂)₅NH₂ |
| Cl | CH₂OH | —CH—CR¹²—S—CZ— | nPn | SO₂NHCO(CH₂)₅NHCO₂-t-butyl |
| Cl | CH₂OH | —CH—CR¹²—S—CZ— | nPn | SO₂NHCO(CH₂)₅NH₂ |
| Cl | CH₂OH | —CH—CR¹²—S—CZ— | nPr | SO₂NHCO(CH₂)₄CH₃ |
| Cl | CH₂OH | —CH—CR¹²—S—CZ— | Bn | SO₂NHCOcyPr |
| Cl | CH₂OH | —CH—CR¹²—S—CZ— | nPr | SO₂NHCOOBu |
| Cl | CH₂OH | —CH—CR¹²—S—CZ— | nBu | SO₂NHCOOBu |
| Cl | CH₂OH | —CH—CR¹²—S—CZ— | iBu | SO₂NHCOOBu |
| Cl | CH₂OH | —CH—CR¹²—S—CZ— | nPn | SO₂NHCOOBu |
| Cl | CH₂OH | —CH—CR¹²—S—CZ— | nPr | SO₂NHCOCH(Ph)₂ |
| Cl | CH₂OH | —CH—CR¹²—S—CZ— | nPr | SO₂NHCOCH₂OEt. |

The alkyl substitutents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which ar modified so that each contains a carbon to carbon double bond or triple bond, respectively, such as vinyl, allyl and 2-butenyl.

Cycloalkyl denotes rings composed of 3 to 8 methlene groups, each which may be substituted or unsubstitued with other hydrocarbon substituents, and include for example cyclopropyl, cyclopentyl, cyclohexyl and 4-methylcyclohexyl.

The alkoxy substituent represents an alkyl group as described above attached through an oxygen bridge.

The aryl substituent recited above represents phenyl or naphthyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl. Abbreviations used in schemes and examples are listed in Table 1.

TABLE 1

| Reagents | |
|---|---|
| NBS | N-bromosuccinimide |
| AIBN | Azo(bis)isobutyronitrile |
| DDQ | Dichlorodicyanoquinone |
| Ac₂O | acetic anhydride |
| TEA | triethylamine |
| DMAP | 4-dimethylaminopyridine |
| PPh₃ | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |
| DIPEA | Diisopropylethylamine |
| TBS-Cl | Tributylsilyl chloride |
| TBAF | tetrabutylammonium fluoride |
| TMSCN | trimethylsilyl cyanide |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |

TABLE 1-continued

| iPrOH | isopropanol |
|---|---|
| HMPA | hexamethylphosphoramide |
| Others: | |
| Phe | phenylalanine |
| rt | room temperature |
| TBDMS | t-butyldimethylsilyl |
| OTf | OSO₂CF₃ |
| Ph | phenyl |
| FAB-MS (FSBMS) | Fast atom bombardment mass spectroscopy |
| NOE | Nuclear Overhauser Effect |
| SiO₂ | Silica gel |
| trityl | triphenylmethyl |
| Bn | benzyl |

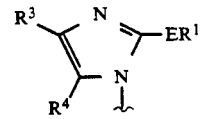

The imidazoles required in for alkylation to the substituted benzyl element can be prepared by a number of methods well known in the literature including those described in EPO publications 253,310 and 324,377 by DuPont and EPO publication by Merck 401,030.

PART II: Preparation of substituted methylphenylthiophenes and furan derivatives and alkylation with the heterocycles described in Part I.

The desired bromomethylphenyl thiophene necessary for the constuction of 3,4-disubstituted thiophenes of formula I, where X¹—X²—X³X⁴=—CH—S—CH—CZ— and Z=tetrazolyl are prepared as illustrated in scheme II-1. Palladium (O)-catalyzed coupling of p-tolyltrimethyltin with 3,4-dibromothiophene in refluxing toluene or DMF at 70°-80° C. for 12 to 24 hours provides 3-bromo-4-tolylthiophene. This bromide could be displaced with cyanide using copper (I)-cyanide in hot quinoline. The nitrile is converted to the trityl protected tetrazole in a three step procedure using trimethyltin azide in refluxing toluene followed by treatment with acid and finally protection with triphenylmethyl chloride in the presence of triethyl amine using CH₂Cl₂ or CHCl₃ as solvent. The protected tetrazole compound can be treated with N bromosuccinimide in refluxing carbontetrachloride in the presence of a catalytic amount of AIBN or benzoylperoxide to provide the necessary bromomethylphenyl thiophenes. Substitution in the 2 position of the thiophene ring can be accomplished by reaction with nBuLi or tBuLi followed by quenching with an appropriate electrophile. Again reaction with N-bromosuccinamide, as before, provides the required bromomethylphenyl thiophenes.

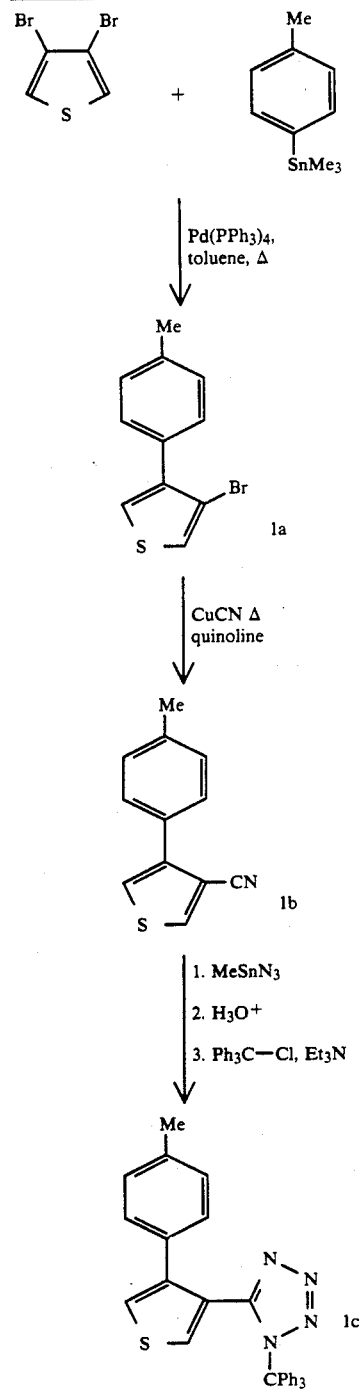

SCHEME II-1

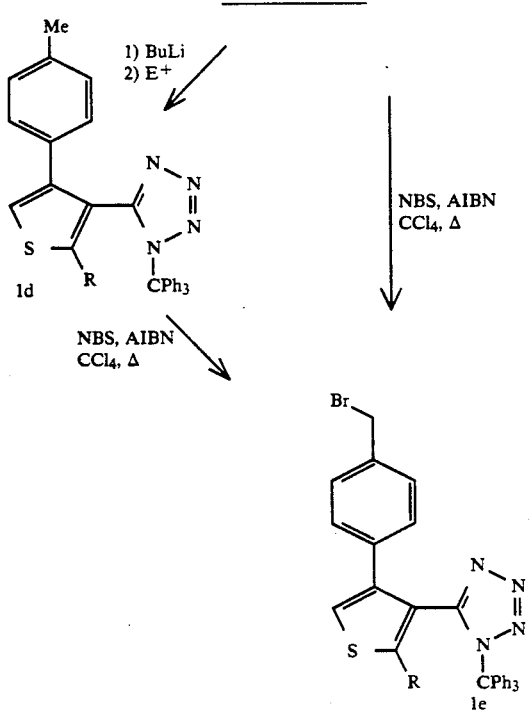

The desired bromomethylphenyl thiophene necessary for the constuction of 3,4-disubstituted thiophenes of Formula I, where $X^1-X^2-X^3-X^4=$—CH S—CH—CZ— and Z=$SO_2NHCOR^7$, are prepared as illustrated in scheme II2. Sequential dianion formation of 2a with nBuLi or tBuLi in THF at $-20°$ C., followed by quenching with TMSCl provides 2b. Treatment with strong base such as nBuLi, LDA or tBuLi, followed by quenching with $Br_2$ affords the bromo thiophene derivative 2c. Palladium catalyzed cross-coupling of 2c with p-tolyltrimethyltin using $PdCl_2(PPh_3)_2$ in hot DMF or $Pd(PPh_3)_4$ in hot toluene provides 2d. Biaryl compound 2d can be treated with N-bromosuccinimide in refluxing carbontetrachloride or benzene in the presence of a catalytic amount of AIBN or benzoylperoxide to provide the necessary bromomethylphenyl thiophenes.

SCHEME II-2

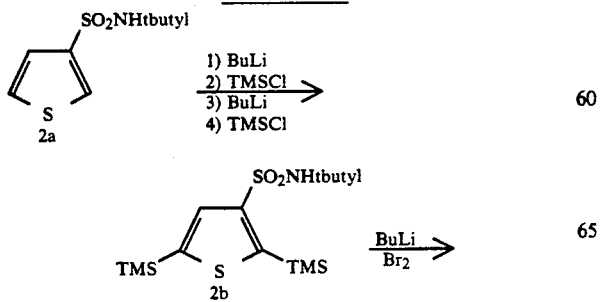

—continued
SCHEME II-2

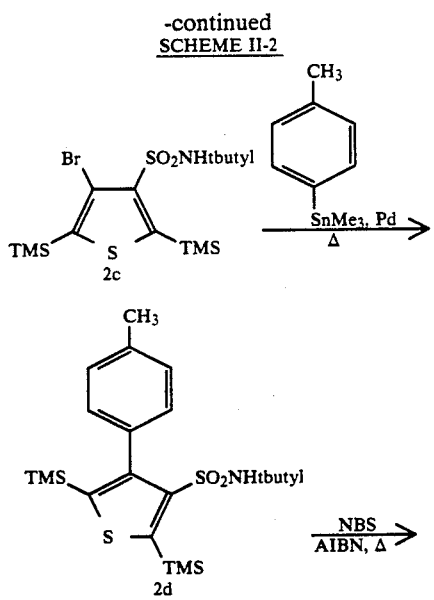

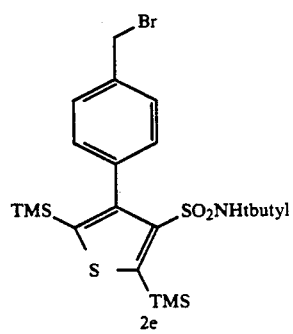

The desired methanesulfonylmethylphenyl thiophenes and furans necessary for the constuction of 2,3-disubstituted thiophenes and furans (Y=O or S) of formula I, where $X^1-X^2-X^3-X^4=-CH-CH-S-CZ-$ and Z=tetrazolyl, are prepared as illustrated in scheme II-3. 2-Cyanothiophene and 2-cyanofuran are converted to their respective protected tetrazoles by reaction with trimethyltin azide in refluxing toluene followed by treatment with dilute mineral acid and finally protection with triphenylmethyl chloride in the presence of triethyl amine in a chlorinated solvent. Reaction of the heterocycle with a strong base such as nBuLi followed by quenching with trimethylsilyl chloride fixes a trimethyl silyl group in the 5-position. Again reaction with a strong base (tBuLi, nBuLi or LDA), this time, followed by quenching with trimethyltin chloride provides the protected tetrazolylaryltrimethyltin derivative. Palladium catalyzed cross coupling with methyl p-iodobenzoate in refluxing toluene or hot DMF for several hours is followed by lithium aluminum hydride reduction and conversion of the subsequent alcohol to the mesylate with methanesulfonyl chloride and triethyl amine.

SCHEME II-3

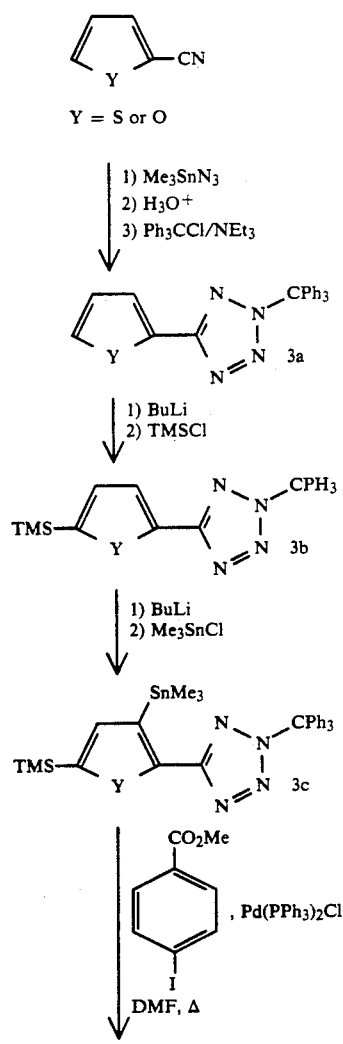

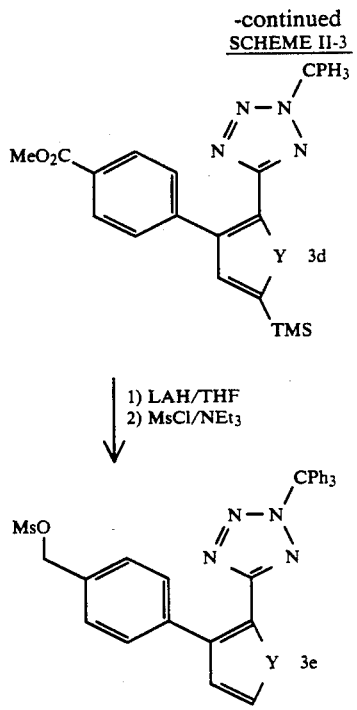

The desired bromomethylphenyl thiophenes and furans necessary for the constuction of 2,3-disubstituted thiophenes and furans (Y=O or S) of formula I, where $X^1-X^2-X^3-X^4=-CR^{11}-CR^{12}-S-CZ-$ and $Z=SO_2NHCOR^7$ and $R^{11}=R^{12}=H$, are prepared as illustrated in scheme II-4. Palladium(O)-catalyzed coupling of p tolyltrimethyltin with a 3-bromothiophene or furan derivative in refluxing toluene provides the 3-tolylthiophene or 3-bromothiophene or furan. If the 5-position of the furan or thiophene is unsubstituted it is protected as was carried out in scheme II-3 with a trimethylsilyl group. Reaction with a strong base such as nBuLi, generating the anion at the 2-position, is followed by successive quenching with $SO_2(g)$ followed by N-chlorosuccinamide. The resultant sulfonyl chloride is reacted with tbutyl amine in $CH_2Cl_2$ and is followed by benzylic bromination with N-bromosuccinimide utilizing AIBN or benzoylperoxide as a radical intiator to afford the desired bromomethylphenyl thiophenes and bromomethylphenyl furans.

SCHEME II-4

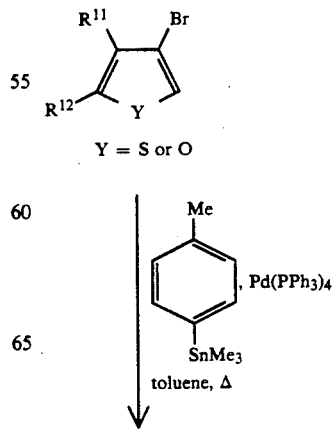

-continued
SCHEME II-4

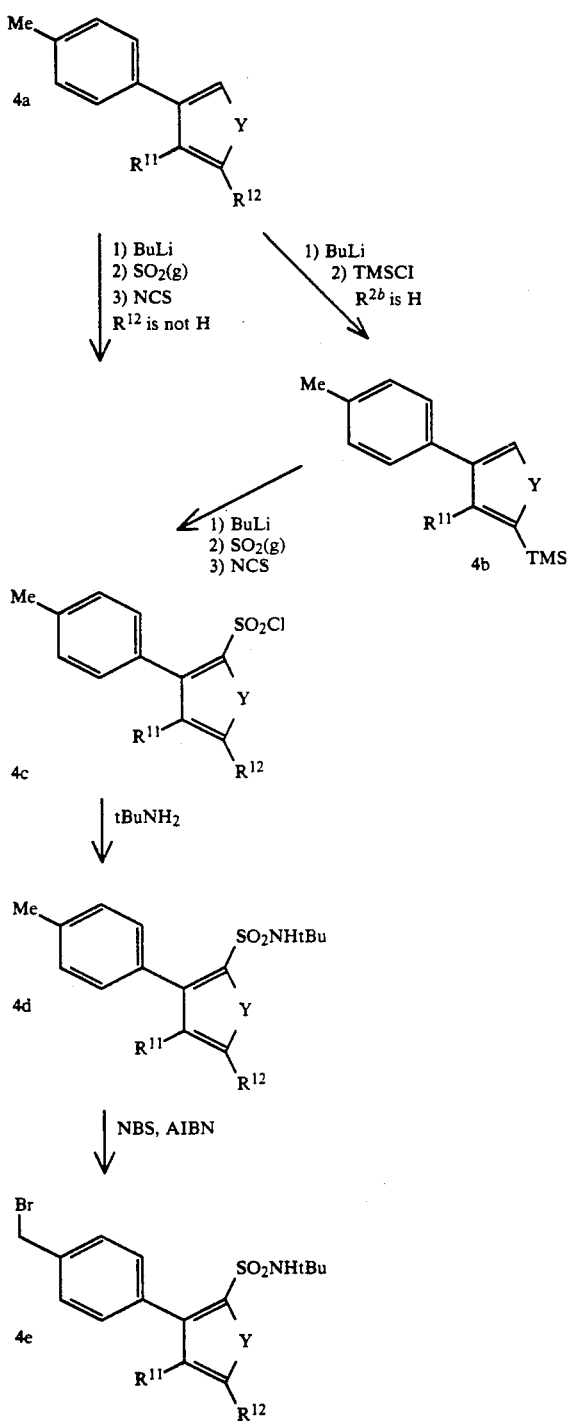

An alternative synthesis for the desired 3-(4-bromomethylphenyl) thiophenes and furans necessary for the constuction of 2,3-disubstituted thiophenes and furans of the 2,3 disubstituted thiophenes and furans (Y=O or S) of formula I, where $X^1—X^2—X^3—X^4=—CR^{11}—CR^{12}—S—CZ—$ and $Z=SO_2NHCOR^7$ and $R^{11}=R^{12}=H$, is illustrated in scheme II-5. 2 Thiophenesulfonyl chloride and 2-furansulfonyl chloride are converted to their respective tbutyl sulfonamides by reaction with tbutylamine in $CH_2Cl_2$. The dianion is generated with two equivalents of a strong base such as nBuLi or tBuLi; this is followed by quenching with TMSCl, addition of another equivalent of strong base and finally quenching with $Br_2$. These bromo derivatives are coupled with p-tolyltrimethyl tin in the presence of a catalytic amount of palladium (O) in refluxing toluene or hot DMF. Benzylic bromination using N-bromosuccinimide provides the desired bromomethylphenyl thiophenes and bromomethylphenyl furans.

SCHEME II-5

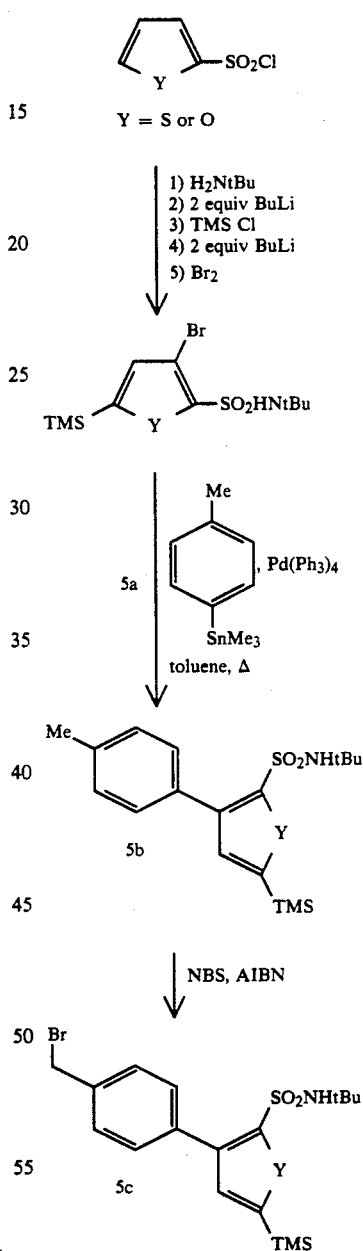

The desired methanesulfonylmethylphenyl thiophenes and furans necessary for the constuction of 2,3-disubstituted thiophenes and furans (Y=O or S) of formula I, where $X^1—X^2—X^3—X^4=—S—CH—CH—CZ—$ and Z=tetrazolyl, are prepared as illustrated in scheme II-6. 3-Cyanothiophene and 3-cyanofuran are converted to their respective protected tetrazole derivatives by reaction with trimethyltin azide in refluxing toluene followed by treatment with dilute mineral acid and finally protection with triphenylmethyl chloride in the presence of triethyl amine. Generation of the anion at the 2-position, using a strong base such as nBuLi, followed by quenching with trimethyltin chloride provides the desired protected tetrazolylaryltrimethyltin derivative. Palladium catalyzed cross coupling with methyl p-iodobenzoate using Pd(PPh3)2Cl2 or Pd(PPh3)4 in refluxing toluene or hot DMF followed by lithium aluminum hydride reduction and treatment of the resultant alcohol with methanesulfonyl chloride and triethyl amine provides the desired methanesulfonylmethylphenyl thiophenes and methanesulfonylmethylphenyl furans.

SCHEME II-6

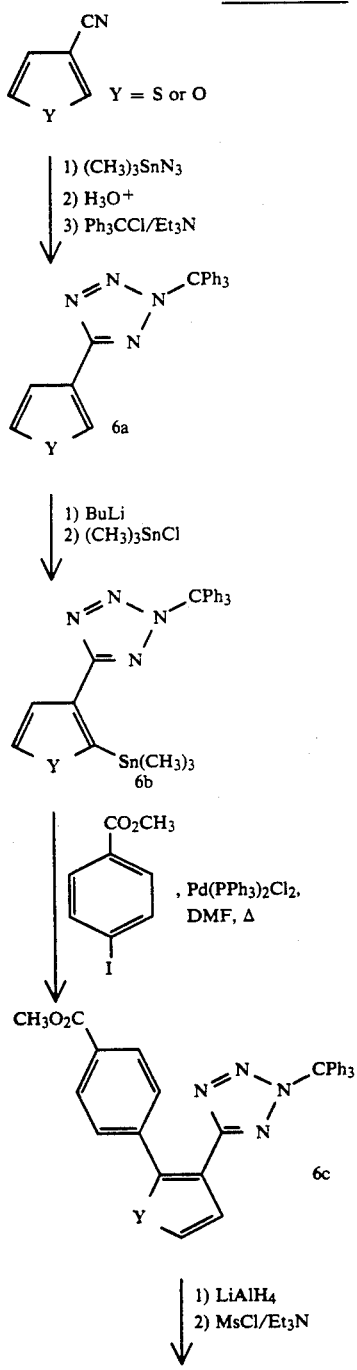

-continued
SCHEME II-6

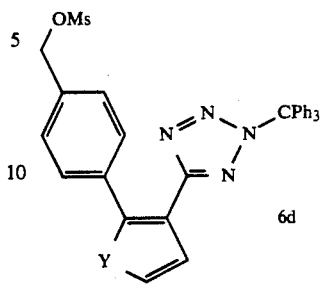

6d

The desired bromomethylphenyl thiophenes and furans necessary for the construction of 2,3-disubstituted thiophenes and furans (Y=O or S) or formula I, where $X^1—X^2—X^3X^4=—S—CH—CH—CZ—$ and $Z=SO_2NHCOR^7$, are prepared are illustrated in scheme II-7. 2,5-Dibromothiophene or 2,5-dibromofuran can be chlorosulfonylated with chlorosulfonic acid to provide sulfonyl chloride 7a. Reaction with tbutylamine, followed by reduction with zinc in acetic acid affords 7c. Dianion generation, using a strong base (nBuLi or tBuLi), followed by quenching with Br2, provides bromo compound 7d. Palladium catalyzed coupling of p-tolytrimethytin with the newly prepared arylbromide in hot DMF or refluxing toluene provides biaryl compound 7e. Treatment of 7e with N-bromosuccinimide in the presence of a catalytic amount of AIBN or benzoylperoxide in refluxing carbontetrachloride or benzene provides the desired bromomethylphenyl thiophenes and bromomethylphenyl furans.

SCHEME II-7

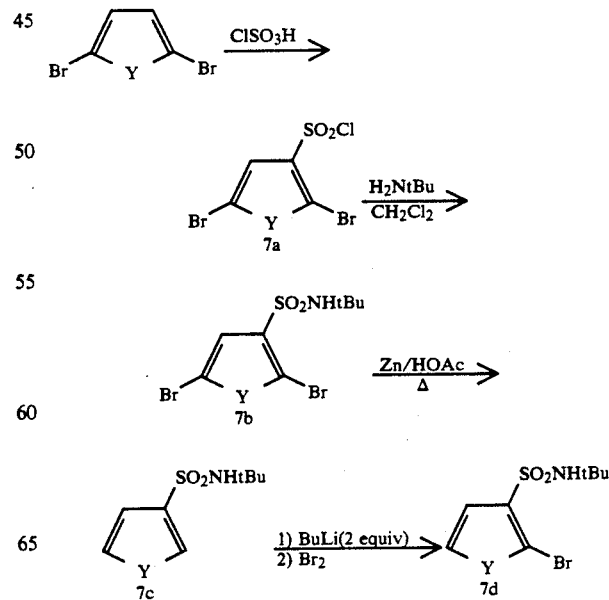

-continued
SCHEME II-7

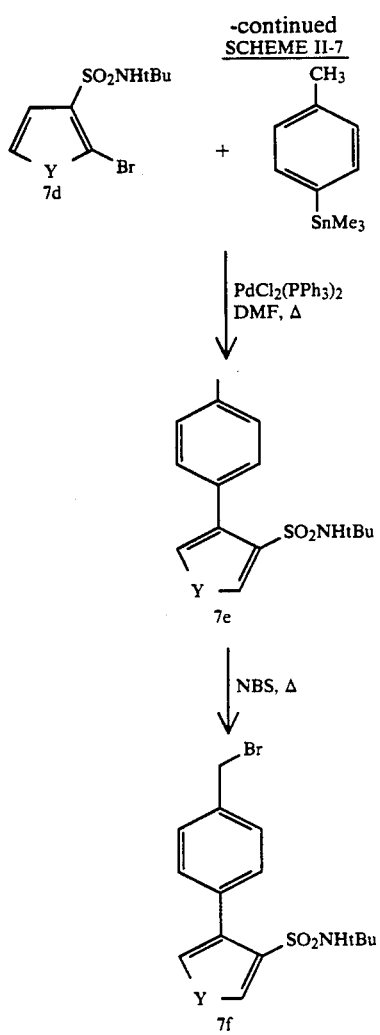

The desired antagonists of formula I (Z=tetrazolyl) are prepared, as illustrated in scheme II-8, by deprotonation of the desired heterocycle, for example 2-butyl-4-chloro-5-[(t-butyldimethysilyloxy)methyl]imidazole ($R^3$=Cl, $R^4$=TBDMSOCH$_2$, $ER^1$=butyl) with sodium hydride in dimethylformamide to generate the sodium salt, Alkylation of the sodium salt with a derivative containing a good leaving group such as the bromomethyl derivative or the methanesulfonyl derivative, is followed by chromatographic separation of the regioisomers if $R^3$ and $R^4$ are not equivalent and deprotection to provide the free tetrazole.

The desired antagonists of formula I (Z=SO$_2$NH-COR$^7$) are prepared, as illustrated in scheme II-9, by deprotonation of the desired heterocycle, for example 2-butyl-4-chloro-5-[(t-butyldimethylsilyloxy)methyl]imidazole ($R^3$=Cl, $R^4$=TBDMSOCH$_2$, $ER^1$=butyl), with sodium hydride in dimethylformamide to generate the sodium salt. Alkylation of the sodium salt with the bromomethyl derivative or the methanesulfonyl derivative followed by chromatographic separation of the regioisomers and deprotection with trifluoroacetic acid, coupling with an activated acid derivative and treatment with 1N NaOH completes the synthesis of the sulfonamide containing thiophene antagonists.

The desired antagonist of formula I, where $X^1$—$X^2$—$X^3$—$X^4$=—$CR^{11}$—$CR^{12}$—S—CZ—, Z=SO$_2$NH-COR$^7$, $R^{11}$ and $R^{12}$ are joined to form an aryl ring, and $R^7$=Ph, is prepared as illustrated in scheme II-10 by deprotonation of the desired heterocycle, for example 2-butyl-4-chloro-5-[(t-butyldimethylsilyloxy)methyl]imidazole ($R^3$=Cl, $R^4$=TBDMSOCH$_2$, $ER^1$=butyl), with sodium hydride in dimethyl formamide to generate the sodium salt. Alkylation of the sodium salt with the benzothiophene derivative, compound 4e, which is prepared using the chemistry illustrated in scheme II-4, affords 10a after separation of the isomers. As in scheme II-9, deprotection with TFA, followed by coupling to an activated acid derivative and hydrolysis with 1N NaOH if $R^3$ or $R^4$=CH$_2$OH completes the synthesis.

SCHEME II-8

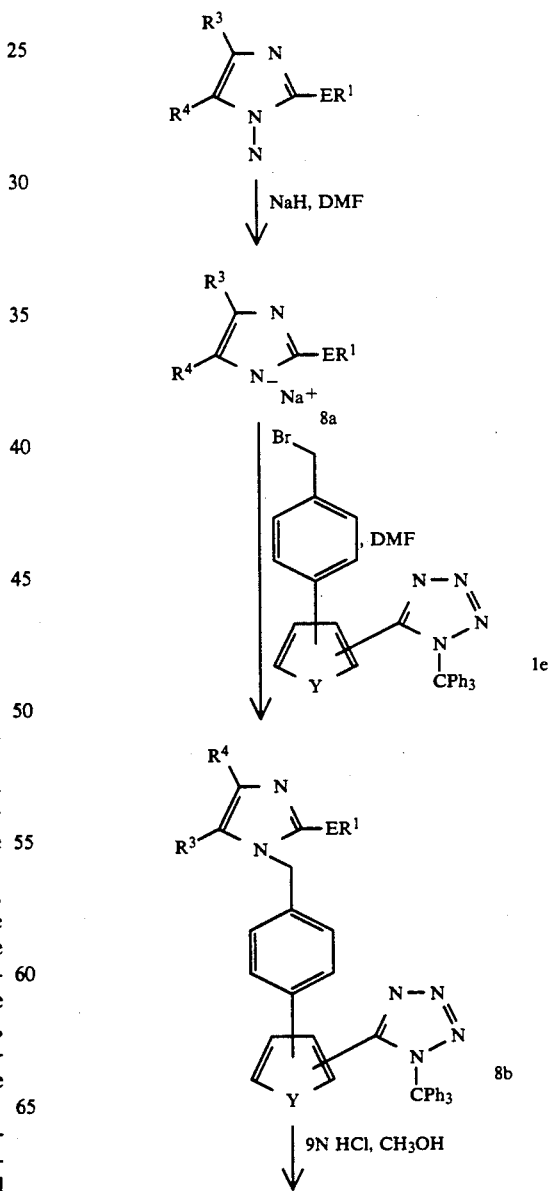

-continued
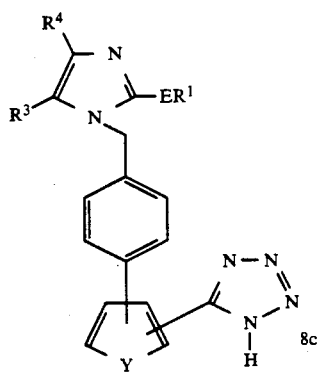
8c
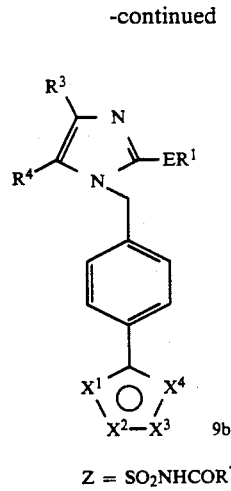
9b
Z = SO₂NHCOR⁷
SCHEME II-9
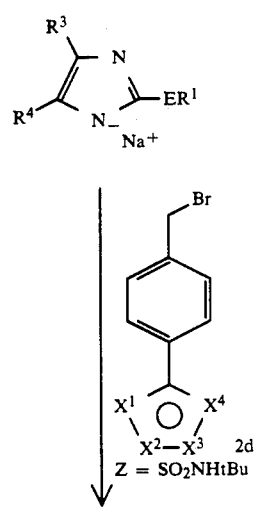
2d
Z = SO₂NHtBu
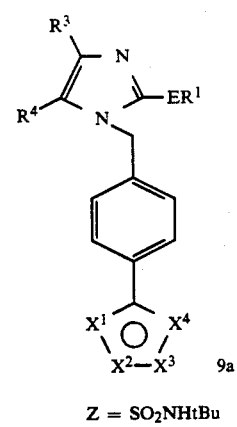
9a
Z = SO₂NHtBu
1) TFA/anisole
2) R⁷COCl/pyridine
  if R³ or R⁴ = CH₂OH, then
3) 1 N NaOH
SCHEME II-10
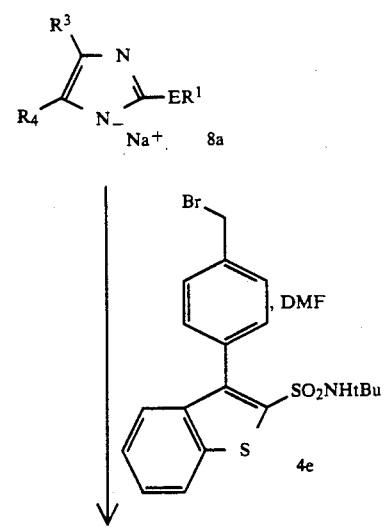
8a
, DMF
4e
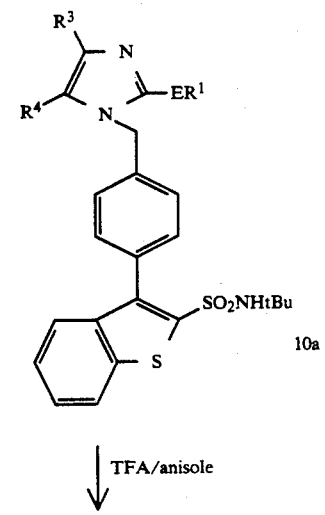
10a
TFA/anisole

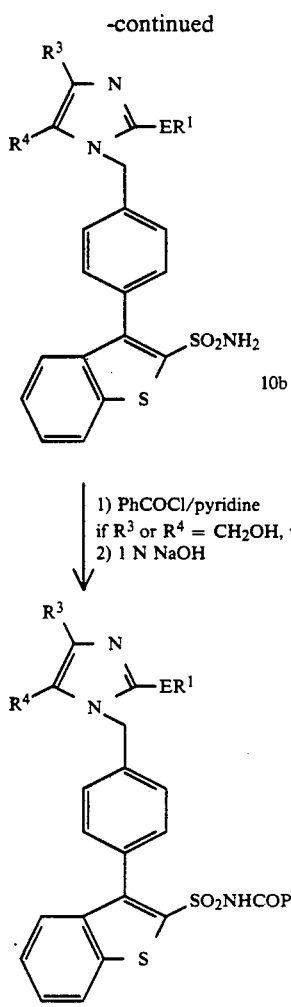

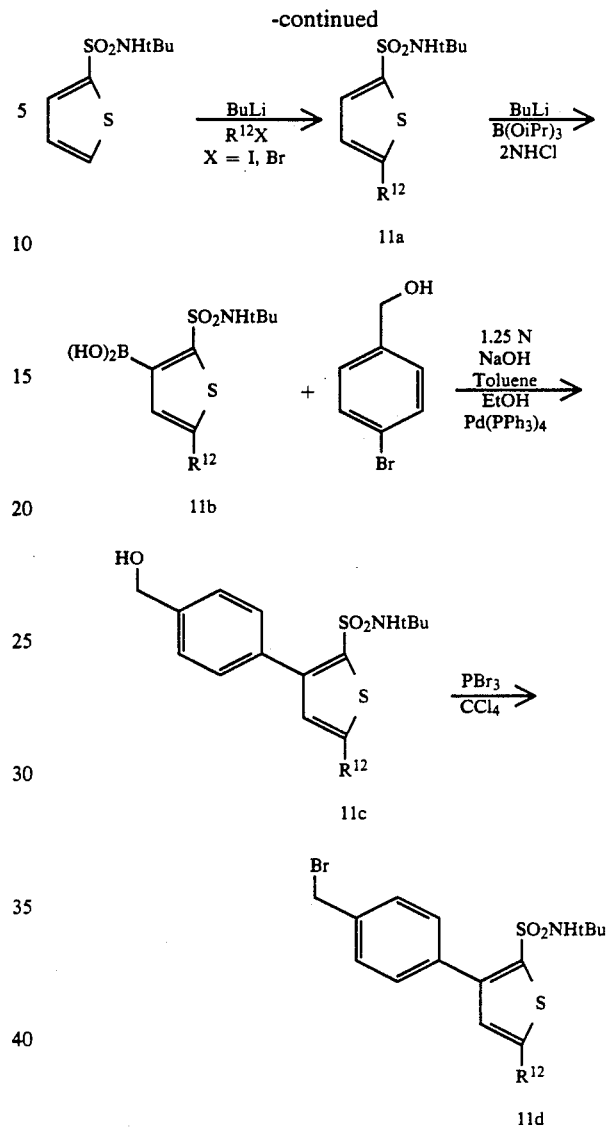

An alternative synthesis for the bromomethylphenyl thiophenes necessary for the construction of substituted thiophenes of formula I, where $X^1{-}X^2{-}X^3{-}X^4{=}{-}CH{=}C(R^{12}){-}S{-}CZ{=}$ and $Z{=}SO_2NHCOR^{14}$ is illustrated in scheme II-11. Alkylthiophene 11a is cleanly prepared by alkylation of the dianion of 2-(tbutylsulfonamido)thiophene, generated with two equivalents of BuLi or LDA, with an appropriate alkylhalide ($R^{12}X$). A second dianion generation, followed by quenching first with triisopropylborate, then with 2N HCl, affords the boronic acid derivative 11b. Palladium catalyzed tcoupling of the 11b with 4-bromobenzyl alcohol provides 11c. The benzyl alcohol is then cleanly converted to the corresponding bromide (11d) with PBr$_3$ or CBr$_4$/PPh$_3$.

This benzyl bromide is used in place of compound 2d in scheme II-9 to complete the synthesis of the antagonist.

Scheme II-12 illustrates a more convergent approach to the synthesis of substituted thiophenes of formula I, where $X^1{-}X^2{-}X^3{-}X^4{=}{-}CH{=}C(R^{12}){-}S{-}CZ{=}$ and $Z{=}SO_2NHCOR^{14}$ palladium catalyzed coupling of boronic acid 11b with a 4-bromobenzyl derivative, such as 12a, provides a nearly complete antagonist. Completion of the antagonist from 12b is illustrated in scheme II-9.

SCHEME II-11

SCHEME II-12

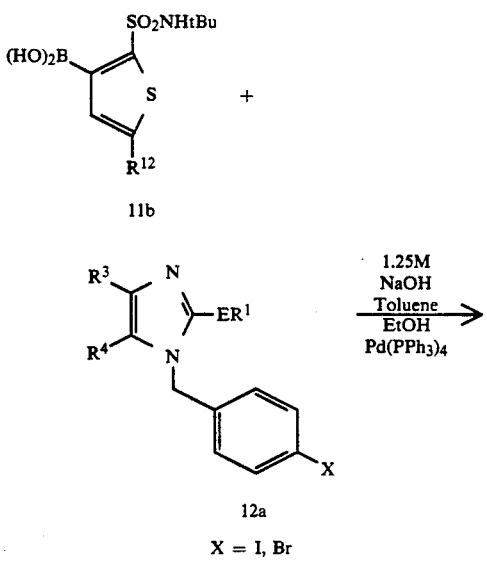

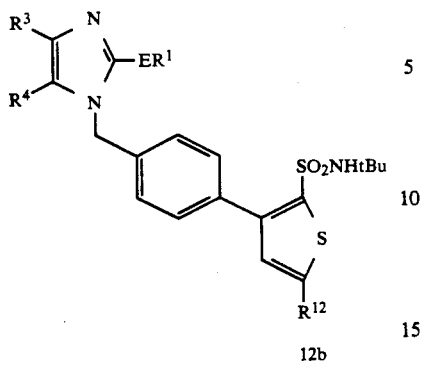

12b

An alternative synthesis for the bromomethylphenyl thiophenes necessary for the construction of substituted thiophenes of formula I, where $X^1—X^2—X^3—X^4=-CH=C(R^{12})-S-CZ=$ and Z=tetrazolyl is illustrated in scheme II-13. Alkylthiophene 13a is prepared by alkylation of the 2-(triphenylmentyltetrazolyl)-thiophene with an appropriate alkylhalide ($R^{12}X$). Directed metalation with BuLi, is followed by quenching with triisopropylborate. The borate ester is gently hydrolyzed with dilute acetic acid to afford the boronic acid derivative 13b. Palladium catalyzed coupling of 13b with 4-bromobenzyl alcohol provides 13c. The benzyl alcohol is then cleanly converted to the corresponding bromide (13d) with $PBr_3$ or $CBr_4/PPh_3$.

This benzyl bromide is used in place of compound 2d in scheme II-9 to complete the synthesis of the antagonist.

Scheme II-14 illustrates a more convergent approach to the synthesis of substituted thiophenes of formula I, where $X^1—X^2—X^3—X^4=—CH=C(R^{12})—S—CZ=$ and Z=tetrazolyl. Palladium catalyzed coupling of boronic acid 13b with a 4-bromobenzyl derivative, such as 12a, provides a nearly complete antagonist. Completion of the antagonist from 14b is illustrated in scheme II-9.

SCHEME II-13

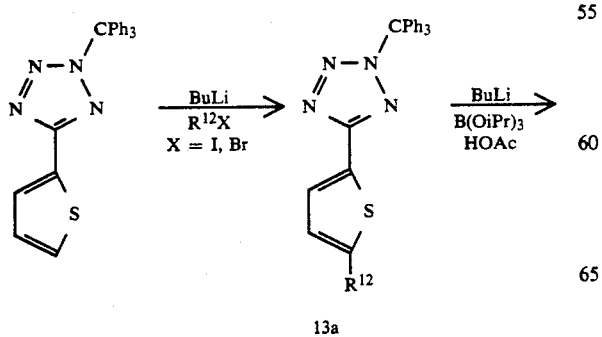

SCHEME II-14

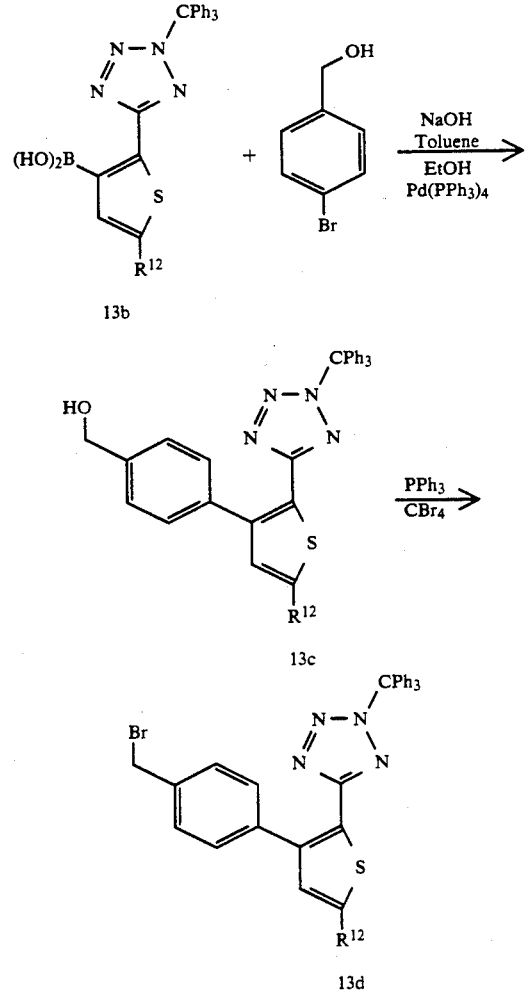

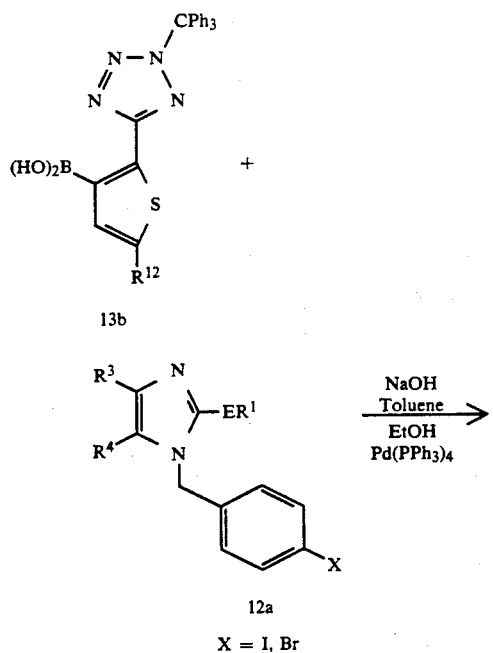

12a
X = I, Br

-continued

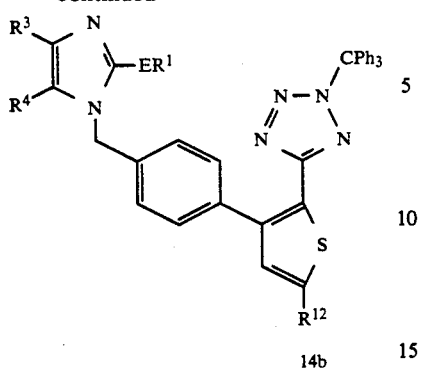

14b

Compounds of formula I, where $X^1$—$X^2$—$X^3$—$X^4$=-CH=C($R^{12}$)-S-CZ=, Z=SO$_2$NHCOR$^{14}$ and $R^{12}$=CH$_2$NR$^{2a}$R$^{2a}$ best prepared as illustrated in scheme II-15. Palladium catalyzed coupling of boronic acid 11b ($R^{12}$=TMS) with 4-bromotoluene provides 15a. Fluoride mediated removal of the trimethylsilyl group is cleanly accomplished using nBu$_4$F in THF. Dianion formation of 15b followed by quenching with a formylating agent, such as DMF, provides the formyl derivative after acid work-up. Benzylic bromination is followed by coupling to the sodium salt of a heterocyle such as an imidazole, to afford 15e. Reductive amination of the aldehyde is then followed by the usual reactions to complete the synthesis of the antagonist.

Alternatively, bromomethyl derivative 16e (scheme II-16) can be prepared and coupled to a heterocyle using previously described synthetic methods. NBS bromination of 2-methyl-5-(tbutylsulfonamido)thiophene provides bromomethyl derivative 16a. The bromomethyl derivative is then reacted with excess amine (HNR$^{2a}$R$^{2a}$), such as morpholine, to afford 16b. Reaction of 16b with two equivalents of a strong base, such as LDA or nBuLi, is followed by addition of bromine to provide 16c. Palladium catalyzed coupling of 16c with 4-(t-butyldimethylsilyloxymethyl) phenyltrimethyltin provides compound 16d. Silyl removal followed by conversion to the corresponding bromide affords 16e.

SCHEME II-15

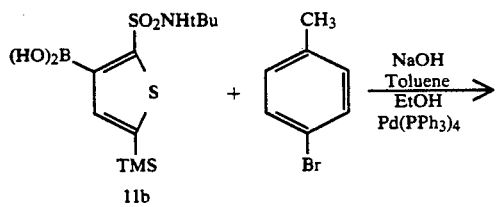

11b

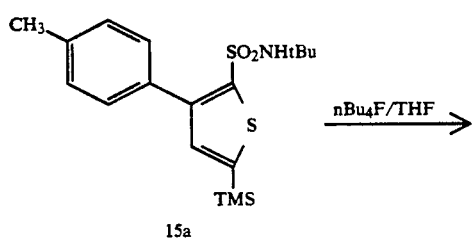

15a

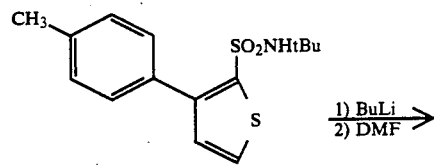

15b

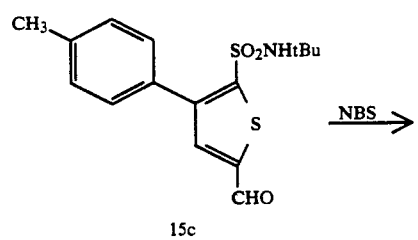

15c

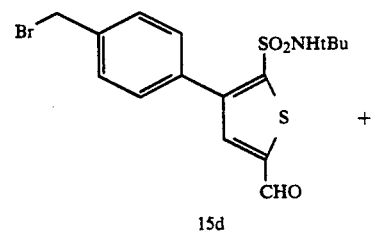

15d

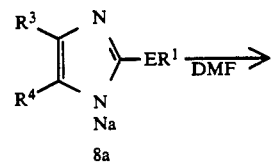

8a

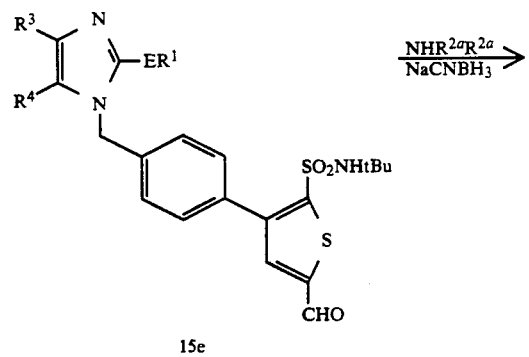

15e

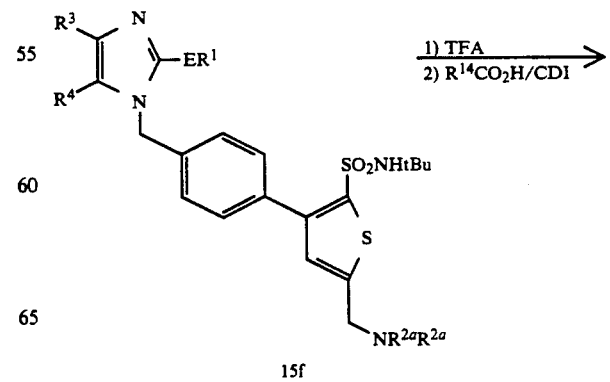

15f

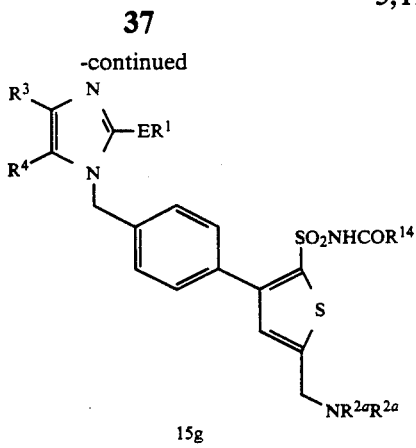

15g

SCHEME II-16

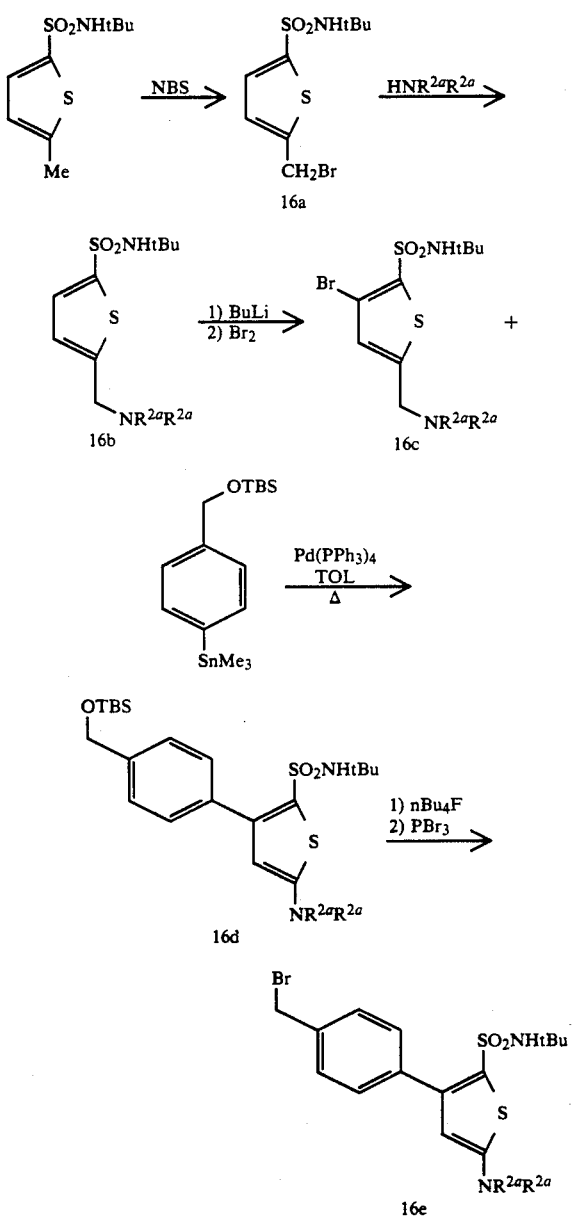

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluenesulfonic, maleic, fumaric, camphorsulfonic. The non toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 mL) homogenized, and then centifuged. The mixture was filtered through a cheesecloth and the supernatant was centrifuged for 30 minutes at 20,000 rpm at 4° C. The pellet thus obtained was resuspended in 30 mL of 50 mM Tris-5 mM $MgCl_2$ buffer containing 0.2% Bovine Serum Albumin and 0.2 mg/mL Bacitracin and the suspension was used for 100 assay tubes. Samples tested for screening were done in duplicate. To the membrane preparation (0.25 mL) there was added $^{125}$I-Sar$^1$Ile8-angiotensin II [obtained from New England Nuclear] (10 mL; 20,000 cpm) with or without the test sample and the mixture was incubated at 37° C. for 90 minutes. The mixture was then diluted with ice-cold 50 mM Tris 0.9% NaCl, pH 7.4 (4 mL) and filtered through a glass fiber filter (GF/B Whatman 2.4" diameter). The filter was soaked in scintillation cocktail (10 mL) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$ angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 mL) there was added $^3$H angiotensin II (50 mM) (10 mL) with or without the test sample and the mixture was incubated at 37° C. for 1 hour. The mixture was then diluted with Tris buffer (4 mL) and filtered through a lass fiber filter (GF/B Whatman 2.4" diameter). The filter was soaked in scintillation cocktail (10 mL) and counted for radioactivity using Packard 2660 Tricarb liquid scintillation counter. The inhibitory concentration (IC$_{50}$ of potential AII antagonist which gives 50% displacement of the total specifically bound $^3$H-angiotensin II was presented as a measure of the efficacy of such compounds as AII antagonists.

The potential antihypertensive effects of the compounds described in the present invention may be evaluated using the methodology described below: Male Charles River Sprague Dawley rats (300–375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent 1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30 minute intervals and the increase in the diastolic blood pressure was recorded before and after drug or vehicle administration.

Using the methodology described above, representative compounds of the invention were evaluated and found to exhibit an activity of at least IC$_{50}$<50 mM thereby demonstrating and confirming the utility of the compounds of the invention as effective AII antagonists.

Thus, the compounds of the invention are useful in treating hypertension. They are also of value in the management of acute and chronic congestive heart failure, in the treatment of secondary hyperaldosteronism, primary and secondary pulmonary hyperaldosteronism, primary and secondary pulmonary hypertension, renal failure and renal vascular hypertension, and in the management of vascular disorders such as migraine or Raynaud's disease. The application of the compounds of this invention for these and similar disorders will be apparent to those skilled in the art.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like.

Pharmaceutical formulations prepared to treat intraocular pressure would typically contain about 0.1% to 15% by weight, and preferably 0.5% to 2.0% by weight of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg per patient per day which can be administered in single or multiple doses. Perferably, the dosage range will be about 2.5 to 250 mg per patient per day; more preferably about 2.5 to 75 mg per patient per day.

The compounds of this invention can also be administered in combination with other antihypertensives and-/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydro chloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan; triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflunisal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg), chlorothiazide (125–2000 mg), ethacrynic acid (15–200 mg), amiloride (5–20 mg), furosemide (5–80 mg), propranolol (20–480 mg), timolol maleate (5–60 mg), methyldopa (65–2000 mg), felodipine (5–60 mg), nifedipine (5–60 mg), and nitrendipine (5–60 mg). In addition, triple drug combinations of hydrochlorothiazide (15–200 mg) plus amiloride (5–20 mg) plus angiotensin II antagonist of this invention (3–200 mg) or hydrochlorothiazide (15–200 mg) plus timolol maleate (5–60) plus an angiotensin II antagonist of this invention (0.5–250 mg) or hydrochlorothiazide (15–200 mg) and nifedipine (5–60 mg) plus an angiotensin II antagonist of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage uniftom is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0 5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereo-typed motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promathazine, fluphenazine and haloperidol.

The following examples illustrate the preparation of the compounds of Formula I and their incorporation into pharmaceutical compositions and as such are not to be considered as limiting the invention set forth in the claims appended hereto.

PREPARATION OF 1-N-ALKYL-2-ALKYLIMIDAZOLES

A general procedure for the synthesis of 1-N-akylated-imidazoles is given below.

A suspension of 1.1 mmol of NaH in 2 mL of dry DMF at 0° C. under nitrogen is treated with 1 mmol of the imidazole as a solid. Immediate evolution of hydrogen could be observed as the imidazole is deprotonated and dissolves. After 30 minutes the solution was warmed to room temperature for a further 30 minutes. To this solution cooled to 0° C. is added a solution of 1 mmol of the appropriate bromomethylphenyl/methanesulfonylmethylphenyl thiophene, benzothiophene or furan, as prepared below, in 1.5 mL of DMF. After 30 minutes, the reaction mixture is warmed to room temperature and stirred overnight. The solution is concentrated in vacuo, and the residue dissolved in 50 mL of EtOAc. The solution is washed with water ($3 \times 10$ mL) and brine ($2 \times 10$ mL). The organic phase is dried over $MgSO_4$, filtered and concentrated in vacuo. The residue is then chromatographed on a silica gel column to separate the regioisomers obtained from N-1 and N-3 alkylation.

EXAMPLE 1

2-Butyl-4-chloro-5-hydroxymethyl-1-[[4-[3-(1H-tetrazol-5-yl)-4-thienyl]phenyl]methyl]imidazole (Compound 1 of Table II)

Step A: Preparation of 3-bromo 4-(4-methylphenyl)thiophene (scheme II-1, compound 1a)

Through a solution of p-tolyltrimethyltin (3.17 g, 12.4 mmol) in dry toluene (8 mL) was bubbled $N_2$ for 5 min to degas the solution. To this was added 3,4-dibromothiophene (2.31 g, 9.56 mmol) and a catalytic amount of $Pd(PPh_3)_4$ (552 mg, 5 mol %). The reaction mixture was brought to reflux (120° C.) and left overnight. The reaction was cooled to rt and the toluene was replaced by EtOAc. The insoluable salts were removed by filtration through a plug of celite. The product was purified by flash chromatography on a silica column eluting with hexane to afford 1.09 g (45%) of the titled compound as a clear, colorless oil.

$^1$H NMR (300 MHz, $CDCl_3$) δ 2.39 (s. $^3$H), 7.21–7.26 (m, 4H), 7.33 (d, $^1$H), 7.38 (d, $^1$H); FAB mass spectrum, m/e 252/254 (m+, calcd for $C^{11}H_9SBr$, 253).

Step B: Preparation of 3-cyano-4-(4-methylphenyl)thiophene (scheme II-1, compound 1b)

To a solution of the product of Step A (329 mg, 1.30 mmol) in quinoline (3 mL) was added CuCN (233 mg, 2.60 mmol) and the solution heated to reflux (235° C.) overnight. The reaction was cooled and $Et_2O$ was added. The solution was washed with 9N HCl and brine, dried over anhydrous $MgSO_4$, and filtered. The product was purified by flash chromatography on a silica column using Hex/EtOAc (35:1) to afford 174 mg (67%) of the titled compound as a light yellow solid.

$^1$H NMR (200 MHz, CDCl$_3$) δ 2.42 (s, 3H), 7.28 (d, 2H), 7.36 (d, 1H), 7.53 (d, 2H), 8.04 (d, 1H); FAB mass spectrum, m/e 199 (m+, calcd for C$_{12}$H$_9$SN, 199).

Step C: Preparation of 3-N-triphenylmethyltetrazolyl 4-(4-methylphenyl)thiophene (scheme II-1, compound 1c)

To a solution of the product of Step B (174 mg, 0.873 mmol) in dry toluene (7 ml) was added Me$_3$SnN$_3$ (1.07 g, 5.22 mmol) and the solution brought to reflux (130° C.). A white solid that is product precipitates. The reaction was left overnight. There was still starting material present and another 363 mg of Me$_3$SnN$_3$ was added. After an additional 5 hours the reaction was cooled to RT. To the reaction was added CH$_2$Cl$_2$ and the reaction was washed with 2N HCl and water, dried over MgSO$_4$ and filtered. The volume was reduced and NEt$_3$ (244 μl, 1.75 mmol) and Ph$_3$CCl (219 mg, 0.787 mmol) were added. After 2 hours Et$_2$O/EtOAc was added to the reaction and the solution was washed with 10% citric acid, 1N NaOH and water, dried over MgSO$_4$ and filtered. The titled compound was isolated in 94% yield, Rf=0.33 (10:1 hex/EtOAc).

$^1$H NMR (300 MHz, CDCl$_3$) δ 2.31 (s, 3H), 6.95 (d, 8H), 7.09 (d, 2H), 7.21–7.34 (m, 10H), 8.00 (d, 1H); FAB mass spectrum, m/e 485 m+1. calcd for C$_{31}$H$_{24}$SN$_4$, 485).

Step D: Preparation of 3-N-triphenylmethyltetrazolyl-4-(4-bromomethylphenyl)thiophene (scheme II-1 compound 1e. R=H)

To a solution of the product of Step C (329 mg, 0.680 mmol) in dry CCl$_4$ (3 mL) was added NBS (133 mg, 0.749 mmol) and a catalytic amount of AIBN. The mixture was heated to reflux (100° C.). After 2 h the reaction was cooled to rt and the insoluable succinimide removed by filtration The solvent was replaced by EtOAc and washed with 1N NaOH and brine, dried over MgSO$_4$ and filtered. The solvent was removed to afford 428 mg (100%) of the crude product as a yellow foam. Rf=0.32 (10:1/Hex:EtOAc).

Step E: preparation of 2-butyl-4-chloro-5-[(t-butyldimethylsilyloxy)methyl]-1-[[4-[3-(N-triphenylmethyltetrazole)-4-thienyl]phenyl]methyl]imidazole (Scheme II-8, compound 8b)

A solution of 2-butyl-4-chloro-5-[(t-butyldimethylsilyloxy)methyl]imidazole was deprotonated with NaH in DMF under a N$_2$ atmosphere. After stirring at rt for 30 min., a solution of the product of Step D in dry DMF was added. After stirring at rt for 5h the DMF was removed at high vacuum and the residue was taken up in CH$_2$Cl$_2$ and the inorganic salts were removed by filtration. The N-1 and N-3 alkylation products were separable by flash chromatography.

Step F: Preparation of 2-butyl-4-chloro-5 hydroxymethyl-1-[[4-[3-($^1$H-tetrazol-5-yl) 4-thienyl]phenyl]methyl]imidazole. (Compound 1 of Table II)

To a solution of the product of Step E (74.0 mg, 0.106 mmol) in methanol (3 mL) was added 9N HCl (10 drops). Within 30 min the reaction was completed. The methanol was removed and the product triturated with Et$_2$O to afford the titled product.

EXAMPLE 2

2-Butyl-4-chloro 5-hydroxymethyl-1-[[4-[2 bromo-3-[[1H-tetrazol-5-yl)-4-thienyl]phenyl]methyl]imidazole (Compound 19 of Table II)

Step A: Preparation of 2-bromo-3-(N-triphenylmethyltetrazol-5-yl)-4-(4-methylphenyl)thiophene (scheme II-1, compound 1d R=Br)

To a solution of the product of Example 1 Step C (101 mg, 0.208 mmol) in dry THF (2 ml) cooled to −78° C. with a dry ice/acetone bath under N$_2$ was added a 1.7M tBuLi solution (0.190 ml, 0.323 mmol). The reaction turned slowly from orange to red then the color dissipated. Another 0.190 ml of tBuLi was added to the reaction. As soon as the red color persisted Br$_2$ (0.40 ml, 0.42 mmol) was added. The product was purified by flash chromatography on a silica column using Hex/EtOAc (35:1). Removal of the solvent afforded 60 mg (51%) of the crude titled product Rf=0.48 (10:1 Hex/EtOAc)

Step B: Preparation of 2-bromo-3-N-triphenylmethyltetrazol-5-yl-4-(4-bromomethylphenyl)thiophene (scheme II-1, compound 1e, R=Br)

To a solution of the product of Step A (22 mg crude) in dry CCl$_4$ (3 mL) was added NBS (7 mg, 0.0448 mmol) and a catalytic amount of AIBN. The reaction was brought to reflux (100° C.). After 2 h the reaction was cooled to rt and the insoluable succinimide was removed by filtration. The solvent was replaced by Et$_2$O/EtOAc and washed with 1N NaOH and brine, dried over MgSO$_4$ and filtered. Removal of the solvent afforded 43 mg (100%) of the crude titled compound. Rf=0.66 (3:1/Hex:EtOAc).

Step C and D: Alkylation and deprotection, following the procedure of Example 1, Steps E through F, provides the titled compound.

EXAMPLE 3

2-Butyl-4-chloro-5-hydroxymethyl-1-[[4-[2-($^1$H-tetrazol-5-yl)-3-thienyl]phenyl]methyl]imidazole (Compound 31 of Table II)

Preparation of 2-[(N-triphenylmethyltetrazol-5-yl]thiophene.(scheme II 3, compound 3a, Y=S)

To a solution of 2-cyanothiophene (1.4 g; 12.8 mmol) in dry toluene (10 ml) was added Me$_3$SnN$_3$ (2.8 g; 13.65 mmol). The mixture was stirred at reflux under N$_2$ for 12 hours. The reaction was cooled to room temperature diluted with CH$_2$Cl$_2$ and washed with 2N HCl soln and H$_2$O. The organic was dried over anhydrous MgSO$_4$ and concentrated in vacuo. The residue, containing the free tetrazole, was dissolved in CH$_2$Cl$_2$ (10 mL) and Ph$_3$CCl (3.2 g; 0.9 equiv.) and NEt$_3$ (3.6 mL) were added. After 20 minutes the mixture was diluted with Et$_2$O/EtOAc and washed with 1N NaOH, 10% citric acid and brine. The organic was dried over anhydrous MgSO$_4$ and concentrated in vacuo. The product was purified by recrystallization from hexanes. The titled compound was isolated in 80% yield, Rf=0.33 (10:1 hex/EtOAc).

$^1$H NMR (200 MHz, CDCl$_3$) δ 7.12–7.21 (comp, 8H), 7.28–7.40 (comp, 8H), 7.42 (dd, 1H), 7.79 (dd, 1H).

Step B: Preparation of 2-trimethylsilyl-5-(N-triphenylmethyltetrazol-5-yl)thiophene (scheme II-3, compound 3b, Y=S)

A solution of the product of Step A (1.00 g, 2.54 mmol) in dry THF (10 ml) under $N_2$ was cooled to −20° C. with a dry ice/acetone bath. To this was added 1.6M nBuLi solution (2.38 ml, 3.81 mmol) by syringe. The reaction mixture turned orange then red and cloudy. The reaction was warmed to −10° C. and stirred for 45 min. The reaction was then cooled to −50° C. and TMSCI (0.322 mL, 2.54 mmol) was added by syringe. The reaction was warmed to 0° C. and quenched with sat'd $NH_4Cl$ solution (5 drops). The solvent was replaced by $Et_2O$/EtOAc and washed with water and brine, dried over $MgSO_4$ and filtered. The product was purified by flash chromatography on a silica column eluting with Hex/EtOAc (40:1). Removal of the solvent affored 849 mg (72%) of the titled product as a slightly orange solid. Rf=0.40 (15:1/Hex:EtOAc).

$^1$H NMR (400 MHz, $CDCl_3$) δ 0.32 (s, 9H), 7.13–7.15 (m, 5H), 7.22 (d, 1H), 7.31–7.33 (m, 10H), 7.82 (d, 1H).

Step C: Preparation of 2-trimethylsilyl 4-trimethyltin-5-(N-triphenylmethyltetrazol-5-yl) thioohene (scheme II-3, compound 3c, Y=S.)

A solution of the product of Step B (752 mg, 1.61 mmol) in dry THF (6 mL) under $N_2$ was cooled to −20° C. with a dry ice/acetone bath. To this was added a 1.6M nBuLi solution (1.53 ml, 2.45 mmol) by syringe. The reaction turned red. As the reaction was warmed to −10° C., the color began to return to orange indicating quenching. The reaction was cooled again to −20° C. and another 1.53 ml of the nBuLi solution was added. The solution turned dark red. The reaction was warmed to −10° C. and allowed to stir at this temperature for 45 min. The reaction was cooled to −60° C. and a solution of $Me_3SnCl$ (844 mg, 4.24 mmol) in dry THF (2 ml was added by cannula. The reaction was warmed to rt and quenched with sat'd $NH_4Cl$ solution. To the flask was added $Et_2O$/EtOAc and the solution washed with 1N NaOH and brine, dried over $MgSO_4$ and filtered. The product was purified by flash chromatography on a silica column eluting with Hex/EtOAc (50:1). Removal of the solvent affored 879 mg (87%) of the titled compound as a white solid. Rf=0.54 (10:1/Hex:EtOAc).

$^1$H NMR (200 MHz, $CDCl_3$) δ 0.13 (s, 9H), 0.35 (s, 9H),.7.12 –7.35 (m, 16H).

Step D: Preparation of 2-trimethylsilyl-4-(4-(1-methoxycarbonyl)phenyl)-5-(N-triphenylmethyltetrazol-5-yl)thiophene (scheme II-3, compound 3d, Y=S)

To a concentrated solution of the product of Step C (194 mg, 0.308 mmol) in dry DMF (1.5 ml) was added p-iodomethylbenzoate (153 mg, 0.583 mmol) and $Pd(PPh_3)_2Cl_2$ (22 mg, 10 mol %). The reaction was heated at 75° C. for several hrs. Because some trityl had been removed by the heat, $NEt_3$ (0.0645 mL, 0.463 mmol) and $Ph_3CCl$ (59 mg, 0.21 mmol) were added. The DMF was replaced by EtOAc and the product was purified by flash chromatography on a silica column eluting with Hex/EtOAc (15:1). Removal of the solvent afforded 116 mg of the titled compound as a white solid. Rf=0.32 (10:1/Hex:EtOAc).

Step E: Preparation of mesylate 3e (scheme II-3, compound 3e, Y=S)

To a solution of the product of step D (116 mg crude) in dry THF (2 ml) under $N_2$ and cooled to 0° C. was added an LAH solution (0.580 ml, 0.580 mmol) by syringe. When the gas evolution subsided, about 5 min, the ice bath was removed and the reaction warmed to RT. To the reaction was added $Et_2O$ then 1 drop water, 1 drop 5.0N NaOH, and 1 drop water. The insoluable salts precipitated. $MgSO_4$ was added and the solids were removed by filtration. Removal of the solvent afforded 142 mg (100% 2 steps) of the crude primary alcohol. Rf=0.41 (2:1/Hex: EtOAc). The primary alcohol (142 mg crude) was dissolved in dry $CH_2Cl_2$ (1.5 mL) under $N_2$ and was cooled to 0° C. To this solution was added $NEt_3$ (0.0595 mL, 0.429 mmol), $CH_3SO_2Cl$ (0.030 mL, 0.388 mmol , and a catalytic amount of 4-dimethylaminopyridine (2 mg, 9 mol %). The reaction was kept at 0° C. After an hour the reaction was warmed to rt and $Et_2O$/EtOAc was added to the reaction. The solution was washed with 10% citric acid. 1N NaOH and brine, dried over $MgSO_4$, and filtered. Removal of the solvent afforded 113 mg (90% for steps D through E) of the crude titled compound. Rf=0.42 (2:1/Hex: EtOAc). The mesylate was used crude without further purification.

Steps F and G: Alkylation with the product of example 3, Step E, and deprotection following the procedure of Example 1, Steps E through F provides the titled compound.

EXAMPLE 4

2-Butyl-4-chloro-5-hydroxymethyl-1-[[4-[2-
1H-tetrazol-5-yl)-3-furanyl]phenyl]methyl]imidazole
(Compound 24 of Table II)

Step A: Preparation of 2-[(N-triphenylmethyl)tetrazol-5-yl]furan (scheme II 3, compound 3a, Y=O)

To a solution of 2 cyanofuran (3.84 g; 41.3 mmol) in dry toluene (30 mL) was added $Me_3SnN_3$ (10 g; 1.2 equiv.). The mixture was stirred at reflux under $N_2$ for 12 hours. The reaction mixture was diluted with $CH_2Cl_2$ and washed with 2N HCl soln and $H_2O$. The organic was dried over anhydrous $MgSO_4$ and concentrated in vacuo. The residue was dissolved in $CH_2Cl_2$ (20 mL) and $NEt_3$ (11.0 mL; 2 equiv.) and $Ph_3CCl$ (10.3 g; 0.9 equiv. were added. After 1 hour the mixture was diluted with $Et_2O$/EtOAc and washed with 10% citric acid, 1N NaOH and brine. The organic was dried over $MgSO_4$ and concentrated in vacuo. The product was crystallized from hexanes. The title compound was isolated in 35% yield, Rf=0.30 (10:1 hex/EtOAc).

$^1$H NMR (200 MHz, $CDCl_3$) δ 6.53 (dd, 1H), 7.08-7.18 (comp, 6H), 7.21-7.40 (comp, 10H), 7.57 (dd, 1H).

Step B: Preparation of 2-trimethylsilyl-5-(N-triphenylmethyltetrazol-5-yl)furan (scheme II-3, compound 3b, Y=O)

A solution of the product of Step A (1.00 g, 2.65 mmol) in dry THF (10 mL) under $N_2$ was cooled to −20° C. with a dry ice/acetone bath. To this was added 1.6M n BuLi solution (2.5 mL, 4.0 mmol). The reaction slowly turned red in color. As the reaction was warmed to −10° C., the color changed to brown and the reaction became cloudy. The reaction was cooled to 50° C. and TMSCl (0.335 mL, 2.64 mmol) was added by syringe. The reaction was warmed to 0° C. and quenched with sat'd NH4Cl solution (6 drops). The solvent was replaced by EtOAc and washed with brine, dried over MgSO4 and filtered. The product was purified by flash chromatography on a silica column eluting with Hex-/EtOAc (40:1). Removal of the solvent afford 590 mg (50%) of the titled product as a white solid. Rf=0.32 (15:1/Hex:EtOAc).

$^1$H NMR (400 MHz, CDCl3) δ 0.29 (s, 9H), 6.69 (d, 1H), 7.04 (d, 1H), 7.12–7.35 (m, 15H).

Step C: Preparation of
2-trimethylsilyl-4-trimethyltin-5-(N-triphenylmethyltetrazol-5-yl)furan (scheme II-3, compound 3c, Y=O)

A solution of the product of Step B (532 mg, 1.18 mmol) in dry THF (5 mL) under N2 was cooled to −20° C. with a dry ice/acetone bath. To this was added 1.6M nBuLi solution (1.13 mL, 1.81 mmol) by syringe. A light red color developed. The reaction was warmed to −10° C. and allowed to stir at this temperature for 45 min. Because the color faded another 1.13 ml of 1.6M nBuLi was added. The reaction was cooled to −60° C. and a solution of Me3SnCl (500 mg, 2.5 mmol) in dry THF (1.5 mL) was added by cannula. The reaction was warmed to rt. To the flask was added Et2O/EtOAc and the solution washed with 1N NaOH, water, and brine, dried over MgSO4 and filtered. The product was purified by flash chromatography on a silica column eluting with Hex/EtOAc (50:1). Rf=0.54 (10:1/Hex:EtOAc). Removal of the solvent affored 520 mg (72%) of the titled compound as a white solid, $^1$H NMR (400 MHz, CDCl3) δ 0.05 (s, 9H), 0.30 (s, 9H), 6.68 (s, 1H), 7.10–7.13 (m, 5H), 7.30–7.32 (m, 10H).

Step D: Preparation of
2-trimethylsilyl-4-(4-(1-methoxycarbonyl)phenyl)-5-(N-triphenylmethyltetrazol-5-yl)furan (scheme II-3, compound 3d, Y=O)

To a concentrated solution of the product of Step C (187 mg, 0.305 mmol) in dry DMF (1.5 mL) was added p iodomethylbenzoate (160 mg, 0.612 mmol) and Pd(PPh3)2Cl2 (22 mg, 10 mol %). The reaction was heated at 75° C. for several hrs. Because some trityl had been removed by the heat, NEt3 (0.043 mL, 0.31 mmol) and Ph3CCl (41 mg, 0.15 mmol) were added. The DMF was replaced by EtOAc and the product was purified by flash chromatography on a silica column eluting with a gradient of Hex/EtOAc (30:1-15:1). Removal of the solvent afforded 100 mg (56%) of the titled compound. Rf=0.23 (10:1/Hex:EtOAc).

$^1$H NMR (400 MHz, CDCl3) δ 0.34 (s, 9H), 3.93 (s, 3H), 6.86 (s, 1H), 7.05–7.07 (m, 6H), 7.24–7.34 (m, 9H), 7.54 (d, 2H), 7.86 (d, 2H).

Step E: Preparation of
3-(4-(1-methanesulfonyloxymethyl)phenyl)-2-(N-triphenylmethyltetrazol5-yl)furan (scheme II-3, compound 3e, Y=O)

To a solution of the product of Step D (100 mg, 0.172 mmol) in dry THF (2 mL) under N2 and cooled to 0° C. was added an 1.0M LAH solution (0.520 mL, 0.520 mmol) by syringe. When the gas evolution subsided the ice bath was removed and the reaction warmed to rt. To the reaction was added Et2O then 1 drop water, 1 drop 5.0N NaOH, and 1 drop water. The insoluable salts precipitated and MgSO4 was added and the solids removed by filtration. The solvent was removed in vacuo and the crude alcohol, Rf=0.35 (2:1/Hex:EtOAc). was used in the next step without further purification. A solution of the primary alcohol in dry CH2Cl2 (1.5 mL) under N2 was cooled to 0° C. To this solution was added NEt3 (0.0527 mL, 0.378 mmol). CH3SO2Cl (0.0266 mL, 0.344 mmol). and a catalytic amount of 4-dimethylaminopyridine (3 mg, 15 mol %). The reaction was kept at 0° C. After an hour the reaction was warmed to rt and Et2O/EtOAc was added to the reaction. The solution was washed with 10% citric acid, 1N NaOH and brine, dried over MgSO4, and filtered. Removal of the solvent afforded 105 mg (96% 2 steps) of the crude titled compound as a bright yellow solid. Rf=0.43 (2:1/Hex:EtOAc). The mesylate was used crude without further purification.

Steps F and G: The titled compound was completed by alkylation followed by deprotection, following the procedures of Example 3, Steps E through F.

EXAMPLE 5

2-Butyl-4-chloro-5-hydroxymethyl-1-[[4-[2-(N-benzoylsulfonamido)-3-benzothienyl]phenyl]methyl]imidazole (Compound 8 of Table II)

Step A: Preparation of
3-(4-methylphenyl)benzothiophene (scheme II-4, compound 4a, Y=S, where $R^{11}$ and $R^{12}$ are joined to from a phenyl ring)

To a solution of 3-bromobenzothiophene (709 mg, 3.33 mmol) and p-tolytrimethyltin (850 mg, 1.0 equiv) in dry toluene (12 mL) under N2 was added Pd(PPh3)4 (192 mg, 5 mol %). The mixture was stirred at reflux for 12 h. The solvent was removed in vacuo and the residue was partially dissolved in hex/EtOAc (10:1) and filtered through a plug of silica. The solvent was removed to afford 658 mg (88%) of crude titled compound. Rf=0.56 (25:1 hex/EtOAc).

Step B: Preparation of
3-(4-methylphenyl)-2-chlorosulfonylbenzothiophene (scheme II-4, compound 4c, Y=S, where $R^{11}$ and $R^{12}$ are joined to form a phenyl ring)

To a solution of the product of Step A (293 mg, 1.308 mmol) in dry THF (5 mL) cooled to 20° C. under N2 was added 1.6M nBuLi (2.44 mL, 3.0 equiv). The reddish-brown anion was stirred at −20° C. for 50 min then cooled to −70° C. and SO2(g) was bubbled in until the anion color disappeared (ca. 5 min). To the now slightly yellow solution was added N-chlorosuccinamide (350 mg, 2 equiv) and the mixture was stirred for 1 h and warmed to rt by removing the ice bath. The reaction mixture was diluted with Et2O/EtOAc and washed with H2O, 5% NaHCO3 soln, and brine The organic was dried over anhydrous MgSO4 and concentrated in vacuo to afford crude titled compound. Rf=0.45 (25:1 hex/EtOAc).

Step C: Preparation of
3-(4-methylphenyl)-2-(N-t-butylsulfonamido)benzothiophene (scheme II-4, compound 4d, Y=S, where $R^{11}$ and $R^{12}$ are joined to form a phenyl rinz).

To a solution of the entire crude product of Step B in dry CH2Cl2 (5 mL) was added tbutylamine (2 mL). The mixture was stirred for 2 days and then diluted with CH2Cl2 and washed with 1N HCl, H2O and brine. The organic was dried over anhydrous MgSO4 and concentrated in vacuo. The product was purified by flash chromatography by first eluting with hex/EtOAc (6:1) and then with $CH_2Cl_2$ to afford 115 mg (25% for step B and C) of the tiltled compound. Rf=0.23 (6:1 hex/EtOAc).

$^1H$ NMR (400 MHz, $CDCl_3$) δ 1.04 (s, 9H), 2.44 (s, 3H), 4.01 (s, 1H), 7.33 (d, 2H), 7.36 (m, 1H), 7.43–7.48 (comp m, 3H), 7.55 (dd, 1H), 7.87 (ddd, 1H); FAB mass spectrum, m/e 360 (m+H, calcd for $C_{19}H_{21}NO_2S_2$, 360).

Step D: Preparation of 3-(4-bromomethylphenyl)-2-(N-t-butylsulfonamido)-benzothiophene (scheme II-4, compound 4e, Y=S, where $R^{11}$ and $R^{12}$ are joined to form a phenyl ring)

To a solution of the product of Step C (115 mg, 0.3203 mmol) in dry benzene (5 mL) was added a catalytic amount of AIBN and N-bromosuccinamide (68 mg, 1.2 equiv). The mixture was stirred at reflux under $N_2$ for 3 h. After cooling to rt the reaction mixture was diluted with $Et_2O$/EtOAc and washed with $H_2O$ and brine. The organic was dried over anhydrous $MgSO_4$ and concentrated in vacuo to afford 147 mg (100%) of the titled compound. Rf=0.18 (6:1 hex/EtOAc). The bromomethyl compound was used crude without further purification.

Step E: Preparation of 2-butyl 4-chloro-5-[(t-butyldimethysilyloxy)methyl]-1-[[4-[2-(N-t-butylsulfonamido)-3-benzothienyl]phenyl]methyl]imidazole (scheme II-10, compound 10a).

To a solution of 2-butyl-4-chloro-5-[(t-butyldimethysilyloxy)methyl]imidazole in dry DMF was added 80% NaH in oil (1.5 equiv). When $H_2$ evolution ceased a solution of the product of Step D in DMF was added. The mixture was stirred at rt for 3 h then quenched with satd $NH_4Cl$ soln and concentrated in vacuo. The residue was dissolved in $CH_2Cl_2$ dried over anhydrous $MgSO_4$, filtered and concentrated in vacuo. A small sample of the reaction mixture was purified by flash chromatography eluting with hex/EtOAc to provide the titled compound in pure form.

Step F: Preparation of 2-butyl-4-chloro-5-hydroxymethyl-3-[[-4-[2-(sulfonamido)-3-benzothienyl]phenyl]methyl]imidazole (scheme II-10, compound 10b)

A solution of the entire product of Step E in TFA and anisole (2 drops) was stirred for 24 h. The TFA was removed at high vacuum and crude sulfonamide remained.

Step G: Preparation of 2-butyl-4-chloro-5-[(benzoyloxy)methyl]-3-[[4-[2-(N-benzoylsulfonamido)-3-benzothienyl]phenyl]methyl]imidazole (scheme II-10, compound 10c)

To a solution of the product of Step F in dry pyridine was added a catalytic amount of DMAP and benzoyl chloride (10 equiv). After stirring for 3 h the pyridine was removed at high vacuum and the residue was taken up in $CH_2Cl_2$ and washed with 5% citric acid soln and $H_2O$. The organic was dried over anhydrous $MgSO_4$ and concentrated in vacuo. The product was purified by flash chromatography.

Step H: Preparation of 2-butyl-4-chloro-5-hydroxymethyl-3-[[4-[2-(N-benzoylsulfonamido)-3-benzothienyl]phenyl]methyl]imidazole (compound 8 of Table II)

To a solution of the product of Step G in MeOH (5 mL) was added 1N NaOH until the mixture started to become cloudy. After stirring at rt for several hours the pH was adjusted to 7.0 and the mixture was concentrated in vacuo. The residue was dissolved in $CH_2Cl_2$ and washed with $H_2O$. The organic was dried over $MgSO_4$ and concentrated in vacuo to provide the titled compound.

EXAMPLE 6

2-Butyl-4-chloro-5-hydroxymethyl-1-[[4-[2-(N-benzoylsulfonamido)-3-thienyl]phenyl]methyl]imidazole (Compound 10 of Table II) and 2-Butyl-4-chloro-5-hydroxymethyl-1-[[-4-[5-trimethylsilyl-2-(N-benzoylsulfonamido) 3-thienyl]methyl]imidazole

Step A: Preparation of 3-bromo-2-t-butylsulfonamido-5-trimethylsilylthiophene. (scheme II-5, compound 5a, Y=S)

Part 1: To a solution of 2-thiophenesulfonyl chloride (1.22 g, 6.70 mmol) in dry $CH_2Cl_2$ (25 mL) at rt was added $tBuNH_2$ (1.55 mL, 2.2 equiv). After stirring at rt overnight the mixture was diluted with ether and washed with 1N HCl, a sat'd solution of $NaHCO_3$ and brine. The organic was dried over anhydrous $MgSO_4$ and concentrated in vacuo to provide 1.42 g (97%) of t-butylsufonamido-2-thiophene, Rf=0.50 (2:1 hex/EtOAc).

Part 2: To a solution of t-butylsulfonamido-2-thiophene (500 mg, 2.28 mmol) in dry THF 5 mL) cooled to 0° C. under a nitrogen atmosphere was added 1.6M nBuLi (4 mL, 6.4 mmol). After stirring for 30 min trimethylsilylchloride (0.64 mL, 2.2 equiv) was added via syringe. The mixture was stirred for 10 min then 1.6M nBuLi (1.5 mL, 2.4 mmol) was added. After stirring for 30 min $BR_2$ ((0.26 mL, 1.19 equiv) was added. The mixture was allowed to warm to rt and diluted with ether and washed with 1N NaOH and brine. The organic was dried over anhydrous $MgSO_4$ and concentrated in vacuo. The product was purified by flash chromatography eluting with hex/EtOAc (8:1) to afford 198 mg (26%) of the titled compound, Rf=0.32 (6:1 hex/EtOAc).

$^1H$ NMR (200MHz, $CDCl_3$) d 0.33 (s, 9H), 1.27 (s, 3H), 5.01 (bs, 1H), 7.11 ( s, 1H).

Step B: Preparation of 3-p-tolyl-2-t-butylsulfonamido-5-trimethylsilylthiophene. (scheme II-5, compound 5b, Y=S)

To a solution of the product of Step A (176 mg, 0.536 mmol) and p-tolyltrimethyltin (205 mg, 1.5 equiv) in dry DMF (0.8 mL) under nitrogen was added $PdCl_2(PPh_3)_2$ (38 mg, 10 mol %). The mixture was stirred under nitrogen at 80° C. for 6 h. The DMF was removed at high vacuum and the residue was partially dissolved in EtOAc and filtered. The filtrate was concentrated in vacuo and the product was purified by flash chromatography eluting with hex/EtOAc (17.5:1) to afford 116 mg (62%) of the titled compound, Rf=0.31 (10:1 hex/EtOAc).

$^1$H NMR (200MHz, CDCl$_3$) d 0.35 (s, 9H), 0.98 (s, 9H), 2.39 (s, 3H), 4.11 (bs, 1H), 7.12 (s, 1H), 7.26 (d, H), 7.50 (d, 2H).

Step C: Preparation of 3-(4-Bromomethylphenyl)-2-t-butylsulfonamido-5-trimethylsilylthiophene. (scheme II-5, compound 5c, Y=S)

To a solution of the product of Step B (207 mg, 0.542 mmol) in dry CCl$_4$ (3 ml), heated to dissolve the reagent, was added NBS (116 mg, 0.651 mmol) and a catalytic amount of AIBN. The reaction was refluxed (110° C.) for 3 h then cooled to rt and the insoluable succinimide was removed by filtration. The solvent was diluted with Et$_2$O/EtOAc and washed with water (2×) and brine, dried over MgSO$_4$ and filtered. The solvent was removed and the crude titled product product (250 mg) dried thoroughly overnight.

Step D: Preparation of 2-Butyl-4-chloro-5-[(t-butyldimethysilyloxy)methyl]-1-[[4-[2-(N-t-butylsulfonamido)-3-thienyl]phenyl]methyl]imidazole [compound 9a, (scheme II-9) where X$^1$—X$^2$—X$^3$—X$^4$=—CH—CH—S—CZ— and Z=SO$_2$NHtBu] and 2-butyl-4-chloro-5-[(t-butyldimethylsilyoxy)methyl]-1-[[4-[5-trimethylsilyl-2-(N-t-butylsulfonamido)-3-thienyl]phenyl]methyl]imidazole [compound 9a, (scheme II-9) where X$^1$—X$^2$—X$^3$—X$^4$=—CH—C(TMS)—S—CZ— and Z=SO$_2$NHtBu]

To a solution of 2-butyl-4-chloro-5-(t-butyldimethysilyloxy)methyl]imidazole, in dry DMF under N$_2$ is added NaH. The reaction is allowed to stir for 30 min. To this is added a solution of the product of step C in dry DMF. After 3 h the reaction was quenched with sat'd NH$_4$Cl solution. The DMF was replaced with EtOAc, dried over MgSO$_4$ and the insoluable salts removed by filtration. The products were purified by flash chromatography on a silica column isolating two products: one where X$^1$—X$^2$—X$^3$—X$^4$=—CH—C(TMS)—S—CZ— and Z=SO$_2$NHtBu and the other where X$^1$—X$^2$—X$^3$—X$^4$=—CH—CH—S—CZ— and Z=SO$_2$NHtBu.

Step E: Preparation of 2-butyl-4-chloro-5-[(benzoyloxy)methyl][[4-[2-(N-benzoylsulfonamido)-3-thienyl]phenyl]methyl]imidazole [compound 9b, (scheme II-9) where X$^1$—X$^2$—X$^3$—X$^4$=—CH—CH-S-CZ- and Z=SO$_2$NHCOPh] and 2-butyl-4-chloro-5-[benzoyloxy) methyl]-1-[[4-[5-trimethylsilyl-2-(N-benzoylsulfonamido)-3-thienyl]methyl]imidazole [Compound 9b, (scheme II-9) where X$^1$—X$^2$—X$^3$—X$^4$=—CH—C(TMS)—S—CZ— and Z=SO$_2$NHCOPh]

Part 1: To the dry product (containing a the TMS group) of Step D was added a catalytic amount of anisole and TFA (2 ml) and the reaction is allowed to stir overnight. The next day when the TFA was removed the reaction became a deep red color. The two products, with and without the TMS group present, were free based by eluting through silica column using CHCl$_3$/MeOH/NH$_4$OH eluant. The two products can be difficult to separate. The mixture can be used in the following step.

Part 2: To the mixture obtained in part 1 (crude) in dry pyridine is added benzoylchloride and a catalytic amount of DMAP. After about 2 h the sides of the flask can be rinsed with additional pyridine and the reaction is allowed to stir another 30 min. The reaction is concentrated then diluted with CH$_2$Cl$_2$ and washed with 10% citric acid (2×) and water, dried over MgSO$_4$, filtered and the solvent removed. The products can be purified by flash chromatography on a silica column or HPLC.

Step F: Preparation of 2-butyl-4-chloro-5-hydroxymethyl[[4-[2-(N-benzoylsulfonamido)-3-thienyl]phenyl]methyl]imidazole (compound 10 of Table II)

The product from Step E was subjected to the same conditions as the product of Example 5, Step H to obtain the titled product.

EXAMPLE 7

2-Butyl-4-chloro-5-hydroxymethyl-1-[[4-[3-(N-benzoylsulfonamido)-2-thienyl]phenyl]methyl]imidazole (Compound 14 of Table II) [compound 9b, scheme II-9, where X$^1$—X$^2$—X$^3$—X$^4$=—S—CH—CH—CZ— and Z=SO$_2$NHCOPh]

Step A: Preparation of 2,5-dibromo-3-t-butylsulfonamidothiophene (scheme II-7, compound 7b, Y=S)

To chlorosulfonic acid (4.5 mL) was added 2,5-dibromothiophene (0.505 g, 2.09 mmol) by syringe. On mixing the reaction turned dark orange-brown. After 10 min the reaction was poured very carefully over ice (100 ml). The solution turned bright yellow. The product was extracted from the water layer using EtOAc/Et$_2$O(3×). The combined organic layers were washed with water and brine, dried over MgSO$_4$ and filtered. The solvent was replaced with dry CH$_2$Cl$_2$ (4.5 ml) and t-butylamine (0.659 mL, 6.27 mmol) was added. The reaction was stirred overnight. The next day the reaction was diluted with more CH$_2$Cl$_2$ and washed with 1N HCl (3×), dried over MgSO$_4$ and filtered. The product was purified by flash chromatography on a silica column eluting with Hex/EtOAc (20:1) to afford 470 mg (60%) of the titled compound, Rf=0.16 (10:$^1$Hex/EtOAc).

$^1$H NMR (400 MHz, CDCl$_3$) 1.25 (s, 9H), 4.75 (s, 1H), 7.30 (s, 1H). FAB mass spectrum, m/e 378 (M+1, calcd for C$_4$H$_{11}$S$_2$O NBR$_2$; 378).

Step B: Preparation of 3-t-butylsulfonamidothiophene (scheme II-7, compound 7c, Y=S)

To a solution of the product of Step A (1.70 g, 4.52 mmol) in 24% by volume glacial acetic acid/water (5 mL) was added Zn dust (1.73 g, 26.6 mmol). The mixture was refluxed (120° C.) overnight. The next day the reaction was cooled, diluted with EtOAc and filtered. Et$_2$O/EtOAc was added and the solution washed with 6N HCl (3×), water, carefully with 5% NaHCO$_3$ (2×) and brine. The solution was dried over MgSO$_4$ and filtered. The solvent was removed to afford 851 mg (86%) of the titled compound, Rf=0.23 (10:1 Hex/EtOAc).

$^1$H NMR (200 MHz, CDCl$_3$) δ 1.25 (s, 9H), 4.42 (s, 1H), 7.31–7.40 (m, 2H), 7.92–7.95 (dd, 1H).

Step C: Preparation of 2-bromo-3-t-butylsulfonamidothiophene (scheme II 7. compound 7d. Y=S)

To a solution of the product of Step B (230 mg, 1.05 mmol) in dry THF (5 mL) cooled to −78° C. in a dry ice/acetone bath under $N_2$ was added 1.6M n-butyllithium (3.28 ml, 5.25 mmol) dropwise. The reaction was warmed to −50° C. then cooled back to −78° C. and $BR_2$ (269 ml, 5.24 mmol) was added. The bath was removed and the reaction was warmed to rt. The reaction was quenched with sat'd $NH_4Cl$ solution. The solvent was replaced with $Et_2O$/EtOAc and the reaction solution washed with water, 1N NaOH, and brine. The solution was dried over $MgSO_4$, filtered and the solvent removed to afford 298 mg (95%) of the titled compound, Rf=0.53 (2:1 Hex/EtOAc).

$^1$H NMR (400 MHz, $CDCl_3$) δ 1.22 (s, 9H), 4.89 (s, 1H), 7.24 (d, 1H), 7.31 (d, 1H).

Step D: Preparation of 2-p-tolyl-3-t-butylsulfonamidothiophene (scheme II-7, compound 7e, Y=S)

To solution of the product of Step C (4.59 mmol, crude) in dry DMF (1 mL) was added p-tolyltrimethyltin (1.77 g, 6.95 mmol) and a catalytic amount of $Pd(PPh_3)_2Cl_2$ (325 mg, 0.463 mmol). The reaction was heated at 75°–80° C. for 5 h. The reaction was cooled to rt and the solvent replaced with EtOAc and filtered. The product was purified by flash chromatography on a silica column eluting with a gradient of Hex/EtOAc (25:1-15:1) to afford 1.01 g (71%) of the titled compound. Rf=0.49 (3:1 Hex/EtOAc).

$^1$H NMR (200 MHz, $CDCl_3$) δ 0.98 (s, 9H). 2.40 (s, 3H), 4.01 (s. 1H), 7.24 (d. 1H). 7.26 (d, 1H), 7.48 (d, 2H), 7.54 (d, 2H); FAB mass spectrum, m/e 310 (M+1, calcd for $C_{15}H_{19}S_2O_2 N$, 310).

Step E: Preparation of 2-(4-bromomethylphenyl)-3-t-butylsulfonamidothiophene (scheme II-7, compound 7f, Y=S)

To a solution of the product of Step D (201 mg, 0.651 mmol) under $N_2$ in dry $CCl_4$ (2.5 mL) was added NBS (130 mg, 0.730 mmol) and a catalytic amount of AIBN. The reaction mixture was brought to reflux (110° C.). After 5 h the reaction was cooled to rt and the insoluable succinimide was removed by filtration. The solvent was replaced with $Et_2O$/EtOAc and washed with water (2×) and brine, dried over $MgSO_4$ and filtered. The solvent was removed and the crude reaction product dried thoroughly under vacuum.

Step F: Preparation of 2-butyl-4-chloro-5-[(t-butyldimethylsilyloxy)methyl]-1-[[4-[3-(N-t-butyllsulfonamido)-2-thienyl]phenyl]methyl]imidazole [compound 9a, scheme II-9, where $X^1$—$X^2$—$X^3$—$X^4$=—S—CH—CH—CZ— and Z=$SO_2$NHtBu]

To a solution of 2-butyl-4 chloro-5-[(t-butyldimethylsilyloxy)methyl]imidazole in dry DMF under $N_2$ is added NaH. The reaction is allowed to stir for 30 min. To this is added a solution of the product of Step E (crude) in dry DMF. After about 5 h the reaction is quenched with sat'd $NH_4Cl$ solution. The DMF is replaced with $Et_2O$/EtOAc, dried over $MgSO_4$ and the insoluable salts removed by filtration. The product was purified by flash chromatography on a silica column.

Step G: Preparation of 2-Butyl-4-chloro-5-[(benzoyloxy)methyl][4-[3-(N-benzoylsulfonamido)-2-thienyl]phenyl]methyl]imidazole [compound 9b, scheme II-9, where $X^1$—$X^2$—$X^3$—$X^4$=—S—CH—CH—CZ— and Z=$SO_2$NHCOPh Part 1: To dry product of Step F is added anisole (2 drops) and TFA and the reaction is allowed to stir overnight. The next day the TFA is removed and the reaction became a deep red color. The product can be purified by flash chromatography on a silica column. Removal of the solvent affords the primary sulfonamide.

Part 2: Acylation with benzoylchloride was carried out following the procedure used in part 2, Step E of Example 6.

Step H: Preparation of 2-butyl-4-chloro-5-[(benzoyloxy)methyl]-[[4-[3-(N-benzoylsulfonamido)-2-thienyl]phenyl]methyl]-imidazole. (compound 14 of Table II).

The product of Step G, part 2, was subjected to the same condition as the product of Example 5, Step H, to obtain the titled compound.

EXAMPLE 8

A representative procedure for the preparation of compounds of Structure 9a. Scheme II-9, where $X^1$—$X^2$—$X^3$—$X^4$=—CH=C($R^{12}$)—S—CZ= and Z=$SO_2$NHtBu

Step 1: Preparation of 2-pentyl-5-(t-butylsulfonamido)thiophene (scheme II 11, compound 11a, $R^{12}$=($CH_2$)$_4CH_3$).

To a solution of 2-(t-butylsulfonamido)thiophene (3.42 g, 15.6 mmol) in anhydrous THF coole to −78° C. under $N_2$ was added 2.5M n-BuLi (15.6 mL, 2.5 equiv). The reaction was warmed to −20° C. over 3.5 h After stirring at −20° C. for an addional h, iodopentane (2.4 mL, 1.2 equiv) was added. The ice bath was removed and the reaction was stirred at rt overnight. The next day the reaction was quenched with sat'd $NH_4Cl$ solution and the THF was removed in vacuo. The residue was extracted with $Et_2O$/EtOAc and washed with water and brine. The organic was dried over anhydrous $MgSO_4$ and concentrated in vacuo. The product was purified by flash chromatography on a silica column eluting with Hex/EtOAc (15:1). Removal of the solvent afforded 2.72 g (60%) of the titled compound as a yellow oil. Rf=0.4 (6:1 Hex/EtOAc).

$^1$H NMR (200 MHz, $CDCl_3$) δ 0.91 (t, 3H), 1.28 (s, 9H), 1.33 (m, 4H), 1.68 (bt, 2H), 2.81 (t, 2H), 4.63 (s, 1H), 6.69 (d, 1H), 7.41 (d, 1H).

The following table lists additional compounds (11a, scheme II-11) prepared using the procedure described above. Any variation from the above procedure is noted in the comment column.

| | | Compounds 11a, Scheme II-11 | | |
|---|---|---|---|---|
| $R^{12}$ | $R^{12}$X | % Yield | Rf (solvent) | Comments |
| $CH_3$ | $ICH_3$ | 49 | 0.44 (3:1 Hex/EtOAc) | *, white solid, ↑ |
| $CH_2CH_3$ | $ICH_2CH_3$ | 84 | 0.47 (3:1 Hex/EtOAc) | *, oil |

Compounds 11a, Scheme II-11

| $R^{12}$ | $R^{12}X$ | % Yield | Rf (solvent) | Comments |
|---|---|---|---|---|
| (CH$_2$)$_2$CH$_3$ | I(CH$_2$)$_2$CH$_3$ | 65 | 0.52 (2:1 Hex/EtOAc) | *, oil |
| (CH$_2$)$_3$CH$_3$ | I(CH$_2$)$_3$CH$_3$ | 62 | 0.32 (6:1 Hex/EtOAc) | *, yellow oil, @ |
| CH$_2$CH(CH$_3$)$_2$ | ICH$_2$CH(CH$_3$)$_2$ | 44 | 0.37 (6:1 Hex/EtOAc) | *, yellow oil, # |
| (CH$_2$)$_4$CH$_3$ | I(CH$_2$)$_4$CH$_3$ | 60 | 0.40 (6:1 Hex/EtOAc) | *, yellow oil |
| CH$_2$Ph | BrCH$_2$Ph | ~70 | 0.49 (3:1 Hex/EtOAc) | taken on crude |
| Si(CH$_3$)$_3$ | ClSi(CH$_3$)$_3$ | 60 | 0.36 (6:1 Hex/EtOAc) | *, solid, @ |

* The high field NMR spectrum and FAB mass spectrum are consistant with the stucture assigned.
Yield is based on recovered starting material.
@ A 1.5M LDA solution was substituted for N-BuLi.
† MPLC purification was necessary.

Step 2: Preparation of boronic acid derivative 11b (scheme II-11, compound 11b, $R^{12}$=(CH$_2$)$_4$CH$_3$).

To a solution of 2-pentyl-5-(t-butylsulfonamido)thiophene product of Step 1 (2.50 g, 8.65 mmol) in anhydrous THF (15 mL) cooled to −78° C. was added 2.5M n-BuLi (8.7 mL, 2.5 equiv). The mixture was allowed to warm to rt over 4 h and stirred for an additional 30 min. The mixture was cooled back to −60° C. and triisopropyl borate (3.0 mL, 1.5 equiv) was added. The ice bath was removed and the mixture was stirred overnight at rt. The next day the reaction was quenched with 2N HCl (3 mL) and the resulting mixture was stirred for 30 min. The THF was removed under reduced pressure and the residue was taken up into EtOAc. The organic was washed with H$_2$O and brine and dried over MgSO$_4$. Removal of the solvent afforded 3.2 g (crude) of the titled compound as a thick yellow oil.

Step 3: Preparation of 4-[(4 hydroxymethyl)phenyl]-2-pentyl-5-(t-butylsulfonamido)thiophene (scheme II 11, compound 11c, $R^{12}$=(CH$_2$)$_4$CH$_3$).

To a solution of the product from step B (3.2 g, crude) in toluene (60 mL) and 1N NaOH (17 ml) was added 4-bromobenzyl alcohol (4.85 g, 3 equiv) in EtOH (15 mL). To this mixture was added Pd(PPh$_3$)$_4$ (300 mg, 3 mol %). The reaction was stirred at reflux under N$_2$ for 4 h. The reaction was cooled to rt and extracted with Et$_2$O/EtOAc. The organic was washed with H$_2$O and brine, dried over anhydrous MgSO$_4$ and concentrated in vacuo. The product was purified by flash chromatography on a silica column eluting with Hex/EtOAc (2:1). Removal of the solvent afforded 1.97 g (58%) of the titled compound as a slightly yellow solid. Rd=0.24 (2:1 Hex/EtOAc).

$^1$H NMR (200 MHz, CDCl$_3$) δ 0.91 (t, 3H), 1.01 (s, 9H), 1.35 (m, 4H), 1.67 (bm, 3H), 2.82 (t, 2H), 4.13 (s, 1H), 4.75 (s, 2H), 6.77 (s, 1H), 7.44 (d, 2H), 7.60 (9d, 2H).

Step 4: Preparation of 4-[(4-bromomethyl)phenyl]-2-pentyl-5-(t-butylsulfonamido)thiophene (scheme II-11, compound 11d, $R^{12}$=(CH$_2$)$_4$CH$_3$).

To a solution of the product of step 3 (493 mg, 1.25 mmol) in anhydrous CCl$_4$ (4mL) and CH$_2$Cl$_2$ (4 mL) was added PBr$_3$ (0.078 mL, 0.66 equiv). After stirring at rt for 1 h the solvent was removed under reduced pressure and the residue was stripped down from CCl$_4$ several times to remove any residual HBr. The product was purified by flash chromatography on a silica column eluting with Hex/EtOAc (2:1). Removal of the solvent afforded 473 mg (83%) of the titled compound as a slightly yellow solid. Rf=0.72 (2:1 Hex/EtOAc).

$^1$H NMR (200 MHz, CDCl$_3$) δ 0.90 (t, 3H), 0.99 (s, 9H), 1.35 (m, 4H), 1.71 (m, 2H), 2.81 (t, 2H), 4.05 (s, 1H), 4.52 (s, 2H), 6.77 (s, 1H), 7.45 (d, 2H), 7.59 (d, 2H).

The following table lists additional compounds (11d, scheme II-11) prepared using the procedure described above. Any variation from the above procedure is noted in the comment column.

Compounds 11d, Scheme II-11

| $R^{12}$ | Pd Coupling Yield | Rf (solvent) | Comments |
|---|---|---|---|
| CH$_3$ | 27 | 0.67 (2:1 Hex/EtOAc) | *, #, white solid |
| CH$_2$CH$_3$ | 23 | 0.70 (2:1 Hex/EtOAc) | taken on crude |
| (CH$_2$)$_2$CH$_3$ | 52 | 0.44 (1:1 Hex/EtOAc) | *, yellowish solid |
| (CH$_2$)$_3$CH$_3$ | 30 | 0.73 (2:1 Hex/EtOAc) | *, yellowish solid |
| CH$_2$CH(CH$_3$)$_2$ | 28 | 0.25 (2:1 Hex/EtOAc 2x's) | *, yellowish solid |
| (CH$_2$)$_4$CH$_3$ | 58 | 0.40 (6:1 Hex/EtOAc) | *, yellowish solid |
| CH$_2$Ph | 25 | 0.54 (3:1 Hex/EtOAc) | *, #, white solid |
| Si(CH$_3$)$_3$ | 36 | 0.45 (6:1 Hex/EtOAc) | *, @, white solid |

* The high field NMR spectrum and FAB mass spectrum are consistant with the stucture assigned.
The palladium catalyzed coupling was done using anhydrous DMF as solvent with NEt$_3$ as base.
@ 4-bromotoluene was substituted for 4-bromobenzyl alcohol in the palladium coupling (step B) and NBS bromination was used to prepare the corresponding bromide.

DEPROTECTION OF THE TRITYL GROUP ON THE TETRAZOLE RING

To a solution of of the trityl protected product in MeOH is added a catalytic amount of 2N HCl. After about an hour the solvent is removed and the product triturated with Et$_2$O to will afford the free tetrazole.

In cases where $R^4$=CH$_2$OH (Examples: 3, 4, 8, 10, 14, 16), benzoylation of the alcohol function is unavoidable during the benzoylation of the sulfonamide. This requires an additional saponification step.

Examples where $R^4$=CO$_2$H were prepared analogously to the examples with $R^4$=CH$_2$OH using an appropriate 5-carbomethoxyimidazole derivative in the alkylation step. Saponification of the ester ($R^4$=$CO_2Me$) to the acid ($R^4$=$CO_2H$) is carried out in the final step.

The compounds shown in Table II can be prepared using the procedures outlined above:

TABLE II

[Structure: imidazole with $R^1$, $R^3$, $R^4$ substituents, N-linked to benzyl group with para-substituent being a 5-membered oxygen-containing ring with positions $X^1, X^2, X^3, X^4$ around O]

| # | $R^1$ | $R^3$ | $R^4$ | $-X^1-X^2-X^3-X^4-$ | $R^{12}$ | Z |
|---|---|---|---|---|---|---|
| 1 | n-butyl | Cl | $CH_2OH$ | $-CH-S-CH-CZ-$ | | 1H-tetrazol-5-yl |
| 2 | n-butyl | Cl | $CO_2H$ | $-CH-S-CH-CZ-$ | | $SO_2NHCOPh$ |
| 3 | n-propyl | Cl | $CH_2OH$ | $-CH-S-CH-CZ-$ | | $SO_2NHCOPh$ |
| 4 | n-butyl | Cl | $CH_2OH$ | $-CH-S-CH-CZ-$ | | $SO_2NHCOPh$ |
| 5 | n-propyl | Cl | $CO_2H$ | $-CH-S-CH-CZ-$ | | 1H-tetrazol-5-yl |
| 6 | n-propyl | $CF_2CF_3$ | $CO_2H$ | $-CH-S-CH-CZ-$ | | 1H-tetrazol-5-yl |
| 7 | n-butyl | $CF_3$ | $CO_2H$ | $-CH-C(Si(CH_3)_3)-S-CZ-$ | | $SO_2NHCOPh$ |
| 8 | n-butyl | Cl | $CH_2OH$ | fused benzo: $-C=C-S-CZ-$ (with benzene ring) | | $SO_2NHCOPh$ |
| 9 | n-butyl | Cl | $CO_2H$ | fused benzo: $-C=C-S-CZ-$ (with benzene ring) | | $SO_2NHCOPh$ |
| 10 | n-butyl | Cl | $CH_2OH$ | $-CH-CH-S-CZ-$ | | $SO_2NHCOPh$ |
| 11 | n-butyl | Cl | $CO_2H$ | $-CH-CH-S-CZ-$ | | $SO_2NHCOPh$ |
| 12 | n-butyl | $CF_2CF_3$ | $CO_2H$ | $-S-CH-CH-CZ-$ | | 1H-tetrazol-5-yl |
| 13 | n-butyl | Cl | $CO_2H$ | $-S-CH-CH-CZ-$ | | 1H-tetrazol-5-yl |
| 14 | n-butyl | Cl | $CH_2OH$ | $-S-CH-CH-CZ-$ | | $SO_2NHCOPh$ |
| 15 | n-butyl | $NO_2$ | $CO_2H$ | $-S-CH-CH-CZ-$ | | $SO_2NHCOPh$ |
| 16 | n-butyl | Cl | $CH_2OH$ | $-CH-S-C(SO_2NHCOPh)-CZ-$ | | H |
| 17 | n-butyl | $NO_2$ | $CO_2H$ | $-CH-S-CH-CZ-$ | | 1H-tetrazol-5-yl |
| 18 | n-butyl | $CF_3$ | $CO_2H$ | $-CH-S-CH-CZ-$ | | 1H-tetrazol-5-yl |
| 19 | n-butyl | Cl | $CH_2OH$ | $-CH-S-C(Br)-CZ-$ | | 1H-tetrazol-5-yl |
| 20 | n-butyl | Cl | $CO_2H$ | $-CH-S-C(Br)-CZ-$ | | 1H-tetrazol-5-yl |
| 21 | n-butyl | $CF_3$ | $CO_2H$ | $-CH-CH-S-CZ-$ | | 1H-tetrazol-5-yl |
| 22 | n-butyl | $CF_2CF_3$ | $CO_2H$ | $-CH-CH-S-CZ-$ | | 1H-tetrazol-5-yl |
| 23 | n-butyl | Cl | $CO_2H$ | $-CH-CH-O-CZ-$ | | 1H-tetrazol-5-yl |
| 24 | n-butyl | Cl | $CH_2OH$ | $-CH-CH-O-CZ-$ | | 1H-tetrazol-5-yl |
| 25 | n-butyl | Cl | $CO_2H$ | fused benzo: $-C=C-S-CZ-$ (with benzene ring) | | 1H-tetrazol-5-yl |
| 26 | n-butyl | Cl | $CH_2OH$ | fused benzo: $-C=C-S-CZ-$ (with benzene ring) | | 1H-tetrazol-5-yl |
| 27 | n-butyl | $NO_2$ | $CO_2H$ | $-CH-CH-S-CZ-$ | | $SO_2NHCOPh$ |
| 28 | n-butyl | $CF_3$ | $CO_2H$ | $-CH-CH-S-CZ-$ | | $SO_2NHCOPh$ |
| 29 | n-butyl | $CF_2CF_3$ | $CO_2H$ | $-S-CH-CH-CZ-$ | | $SO_2NHCOPh$ |
| 30 | n-butyl | $NO_2$ | $CO_2H$ | $-S-CH-CH-CZ-$ | | $SO_2NHCOPh$ |
| 31 | n-butyl | Cl | $CH_2OH$ | $-CH-CH-S-CZ-$ | | 1H-tetrazol-5-yl |
| 32 | n-butyl | Cl | $CH_2OH$ | $-CH-CR^{12}-S-CZ-$ | Me | $SO_2NHCOPh$ |
| 33 | n-butyl | Cl | $CH_2OH$ | $-CH-CR^{12}-S-CZ-$ | Et | $SO_2NHCOPh$ |
| 34 | n-butyl | Cl | $CH_2OH$ | $-CH-CR^{12}-S-CZ-$ | nPr | $SO_2NHCOPh$ |
| 35 | n-butyl | Cl | $CH_2OH$ | $-CH-CR^{12}-S-CZ-$ | nBu | $SO_2NHCOPh$ |
| 36 | n-butyl | Cl | $CH_2OH$ | $-CH-CR^{12}-S-CZ-$ | iBu | $SO_2NHCOPh$ |
| 37 | n-butyl | Cl | $CH_2OH$ | $-CH-CR^{12}-S-CZ-$ | nPn | $SO_2NHCOPh$ |
| 38 | n-butyl | Cl | $CH_2OH$ | $-CH-CR^{12}-S-CZ-$ | Bn | $SO_2NHCOPh$ |
| 39 | n-butyl | Cl | $CH_2OH$ | $-CH-CR^{12}-S-CZ-$ | $CH_2N(CH_2CH_2)_2O$ | $SO_2NHCOPh$ |
| 40 | n-butyl | Cl | $CH_2OH$ | $-CH-CR^{12}-S-CZ-$ | $CH_2N(CH_2CH_2)_2O$ | $SO_2NHCOCH(Ph)_2$ |

TABLE II-continued

| | | | | | |
|---|---|---|---|---|---|
| 41 | n-butyl | Cl | CH$_2$OH | —CH—CR$^{12}$—S—CZ— | nPr | SO$_2$NHCO(CH$_2$)$_2$OMe |
| 42 | n-butyl | Cl | CH$_2$OH | —CH—CR$^{12}$—S—CZ— | Me | SO$_2$NHCOCH$_2$Ph |
| 43 | n-butyl | Cl | CH$_2$OH | —CH—CR$^{12}$—S—CZ— | Me | SO$_2$NHCOCH(Ph)$_2$ |
| 44 | n-butyl | Cl | CH$_2$OH | —CH—CR$^{12}$—S—CZ— | Et | SO$_2$NHCOCH(Ph)$_2$ |
| 45 | n-butyl | Cl | CH$_2$OH | —CH—CR$^{12}$—S—CZ— | Et | SO$_2$NHCOCH$_2$OEt |
| 46 | n-butyl | Cl | CH$_2$OH | —CH—CR$^{12}$—S—CZ— | nBu | SO$_2$NHCOCH$_2$OEt |
| 47 | n-butyl | Cl | CH$_2$OH | —CH—CR$^{12}$—S—CZ— | nPr | SO$_2$NHCOCH$_2$OBu |
| 48 | n-butyl | Cl | CH$_2$OH | —CH—CR$^{12}$—S—CZ— | nBu | SO$_2$NHCO(CH$_2$)$_2$-cyclopentyl |
| 49 | n-butyl | Cl | CH$_2$OH | —CH—CR$^{12}$—S—CZ— | iBu | SO$_2$NHCOCH$_2$OBu |
| 50 | n-butyl | Cl | CH$_2$OH | —CH—CR$^{12}$—S—CZ— | iBu | SO$_2$NHCOCH$_2$OEt |
| 51 | n-butyl | Cl | CH$_2$OH | —CH—CR$^{12}$—S—CZ— | nPn | SO$_2$NHCOCH$_2$OEt |
| 52 | n-butyl | Cl | CH$_2$OH | —CH—CR$^{12}$—S—CZ— | nPn | SO$_2$NHCOCH$_2$OBu |
| 53 | n-butyl | Cl | CH$_2$OH | —CH—CR$^{12}$—S—CZ— | nPn | SO$_2$NHCO$_2$—N-methylpyrrole |
| 54 | n-butyl | Cl | CH$_2$OH | —CH—CR$^{12}$—S—CZ— | nPr | SO$_2$NHCO$_2$—N-methylpyrrole |
| 55 | n-butyl | Cl | CH$_2$OH | —CH—CR$^{12}$—S—CZ— | nPr | SO$_2$NHCOOCH$_2$CH(Me)$_2$ |
| 56 | n-butyl | Cl | CH$_2$OH | —CH—CR$^{12}$—S—CZ— | iBu | SO$_2$NHCOO(CH$_2$)$_2$OMe |
| 57 | n-butyl | Cl | CH$_2$OH | —CH—CR$^{12}$—S—CZ— | nBu | SO$_2$NHCO(CH$_2$)$_5$NHBoc |
| 58 | n-butyl | Cl | CH$_2$OH | —CH—CR$^{12}$—S—CZ— | nBu | SO$_2$NHCO(CH$_2$)$_5$NH$_2$ |
| 59 | n-butyl | Cl | CH$_2$OH | —CH—CR$^{12}$—S—CZ— | iBu | SO$_2$NHCO(CH$_2$)$_5$NHBoc |
| 60 | n-butyl | Cl | CH$_2$OH | —CH—CR$^{12}$—S—CZ— | iBu | SO$_2$NHCO(CH$_2$)$_5$NH$_2$ |
| 61 | n-butyl | Cl | CH$_2$OH | —CH—CR$^{12}$—S—CZ— | nPn | SO$_2$NHCO(CH$_2$)$_5$NHBoc |
| 62 | n-butyl | Cl | CH$_2$OH | —CH—CR$^{12}$—S—CZ— | nPn | SO$_2$NHCO(CH$_2$)$_5$NH$_2$ |
| 63 | n-butyl | Cl | CH$_2$OH | —CH—CR$^{12}$—S—CZ— | nPr | SO$_2$NHCO(CH$_2$)$_4$CH$_3$ |
| 64 | n-butyl | Cl | CH$_2$OH | —CH—CR$^{12}$—S—CZ— | Bn | SO$_2$NHCOcyPr |
| 65 | n-butyl | Cl | CH$_2$OH | —CH—CR$^{12}$—S—CZ— | nPr | SO$_2$NHCOOBu |
| 66 | n-butyl | Cl | CH$_2$OH | —CH—CR$^{12}$—S—CZ— | nBu | SO$_2$NHCOOBu |
| 67 | n-butyl | Cl | CH$_2$OH | —CH—CR$^{12}$—S—CZ— | iBu | SO$_2$NHCOOBu |
| 68 | n-butyl | Cl | CH$_2$OH | —CH—CR$^{12}$—S—CZ— | nPn | SO$_2$NHCOOBu |
| 69 | n-butyl | Cl | CH$_2$OH | —CH—CR$^{12}$—S—CZ— | nPr | SO$_2$NHCOCH(Ph)$_2$ |
| 70 | n-butyl | Cl | CH$_2$OH | —CH—CR$^{12}$—S—CZ— | nPr | SO$_2$NHCOCH$_2$OEt |

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
|---|---|
| 2-Butyl-4-chloro-5-hydroxymethyl-1-[[4-[3-(1H-tetrazol-5-yl)-4-thienyl]phenyl]methyl]imidazole | 50 |
| Lactose | 149 |
| Magnesium stearate | 1 |
| Capsule (size No. 1) | 200 |

The 2-butyl-4-chloro-5-hydroxymethyl-1-[[4-[3-(1H-tetrazol-5-yl) 4-thienyl]phenyl]methyl]imidazole can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 2-butyl-4-chloro-5-hydroxymethyl-1-[[4-[3-(1H-tetrazol-5-yl)-4-thienyl]phenyl]methyl]imidazole (25 mg). pregelatinized starch USP (82 mg), microcrystalline cellulose (82 mg) and magnesium stearate (1 mg).

C: Combination Tablet

A typical combination tablet would contain, for example. a diuretic such as hydrochlorothiazide (25 mg) and 2-butyl-4-chloro-5 hydroxymethyl[[4-[3-(1H-tetrazol-5-yl)-4-thienyl]phenyl]methyl]imidazole (50 mg) pregelatinized starch USP (82 mg), microcrystalline cellulose (82 mg) and magnesium stearate (1 mg).

D: Suppository

Typical suppository formulations for rectal administration can contain 2-butyl-4-chloro 5-hydroxymethyl-1-[[4-[3-(1H-tetrazol-5-yl)-4-thienyl]phenyl]methyl]imidazole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M. Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 2-butyl-4-chloro-5-hydroxymethyl-1-[[4-[3-(1H-tetrazol-5-yl)-4-thienyl]phenyl]methyl]-imidazole sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of structural formula I

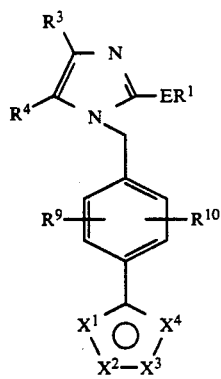

or its pharmaceutically acceptable salt wherein:

R¹ is:
(a) $(C_1-C_6)$-alkyl, $(C_2-C_6)$-alkenyl or $(C_2-C_6)$-alkynyl each of which is unsubstituted or substituted with a substituent selected from the group consisting of:
i) aryl as defined below,
ii) $(C_3-C_7)$-cycloalkyl,
iii) Cl, Br, I, F,
iv) OH,
v) $NH_2$,
vi) $NH(C_1-C_4)$-alkyl,
vii) $N[(C_1-C_4)$-alkyl$]_2$,
viii) $NHSO_2R^2$,
ix) $CF_3$,
x) $COOR^2$, or
xi) $SO_2NHR^{2a}$;

(b) aryl, wherein aryl is defined as phenyl or naphthyl, unsubstituted or substituted with 1 or 2 substituents selected from the group consisting of:
i) Br, I, Cl, F,
ii) $(C_1-C_4)$-alkyl,
iii) $(C_1-C_4)$-alkoxy,
iv) $(C_3-C_7)$-cycloalkyl,
v) $(C_3-C_{10})$-alkenyl,
vi) $(C_1-C_4)$-alkylthio,
vii) OH,
viii) $CO_2H$,
ix) $CO_2-(C_1-C_4)$-alkyl,
x) $NO_2$,
xi) $CF_3$,
xii) $NH_2$,
xiii) $NH[(C_1-C_4)$-alkyl$]$,
xiv) $N[(C_1-C_4)$-alkyl$]_2$, or
xv) $SO_2NR^{2a}R^{2a}$, (c) heteroaryl, wherein heteroaryl is selected from the group consisting of: pyridyl, thienyl, furyl, imidazolyl and thiazolyl, and wherein the heteroaryl is unsubstituted, monosubstituted or disubstituted with substituents selected from the group consisting of:
i) Cl, Br, I, or F,
ii) OH,
iii) SH,
iv) $NO_2$,
v) $(C_1-C_4)$-alkyl,
vi) $(C_2-C_4)$-alkenyl,
vii) $(C_2-C_4)$-alkynyl,
viii) $(C_1-C_4)$-alkoxy,
ix) $CF_3$,
xii) $NH_2$,
xiii) $NH[(C_1-C_4)$-alkyl$]$,
xiv) $N[(C_1-C_4)$-alkyl$]_2$,
xv) $CO_2H$, or
xvi) $CO_2-(C_1-C_4)$-alkyl, or
(d) $(C_1-C_4)$-polyfluoroalkyl;

E is:
(a) a single bond,
(b) $-S(O)_n(CH_2)_x-$, or
(c) $-O-$;

R² is:
(a) H, or
(b) $(C_1-C_6)$-alkyl;

$R^{2a}$ is:
(a) $R^2$,
(b) $CH_2$-aryl, or
(c) aryl;

n is 0 to 2;
s is 0 to 5;
m is 1 to 5;
p is 0 to 3;
x is 1 to 10;

R³ is:
(a) H,
(b) $(C_1-C_6)$-alkyl, $(C_2-C_6)$-alkenyl or $(C_2-C_6)$-alkynyl,
(c) Cl, Br, I, F,
(d) $NO_2$,
(e) $CF_3$,
(f) $(C_1-C_8)$-polyfluoroalkyl,
(g) $C_6F_5$,
(h) CN,
(j) phenyl-$(C_1-C_3)$-alkyl,
(k) phenyl and phenyl-$(C_1-C_3)$-alkyl substituted on the phenyl ring with one or two substituents selected from:
i) $(C_1-C_4)$-alkyl,
ii) $(C_1-C_4)$-alkoxyl,
iii) F, Cl, Br, I,
iv) hydroxyl,
v) methoxyl,
vi) $CF_3$,
vii) $CO_2R^{2a}$,
viii) $NO_2$, or
ix) $SO_2NR^{2a}R^{2a}$;

R⁴ is:
(a) H,
(b) CN,
(c) $(C_1-C_8)$-alkyl,
(d) $(C_3-C_6)$-alkenyl,
(e) $(C_1-C_8)$-polyfluoroalkyl,
(f) $(C_1-C_8)$-polyfluoroalkenyl,
(g) $CF_2CF_3$,
(h) $CO_2R^{2a}$,
(i) phenyl,
(j) phenyl-$(C_2-C_6)$-alkenyl, (k) $-\overset{\overset{\displaystyle O}{\|}}{C}-R^5$, (l) $-(CH_2)_{x-1}-\overset{\overset{\displaystyle OR^6}{|}}{CH}-R^6$, (m) $-(CH_2)_x-O\overset{\overset{\displaystyle O}{\|}}{C}R^7$, (n) —$(CH_2)_x$-S(O)$_n$R$^8$, (o) 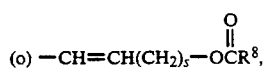—CH=CH(CH$_2$)$_s$—OCR$^8$, (p) 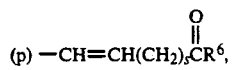—CH=CH(CH$_2$)$_s$CR$^6$, (q) 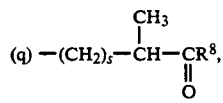—$(CH_2)_s$—CH—CR$^8$, with CH$_3$ and =O (r) 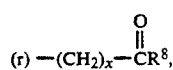—$(CH_2)_x$—CR$^8$, (s) 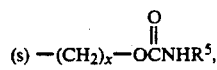—$(CH_2)_x$—OCNHR$^5$, (t) 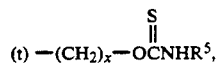—$(CH_2)_x$—OCNHR$^5$, (u) —$(CH_2)_x$-NHSO$_2$R$^5$,
(v) —$(CH_2)_x$-F, R$^5$ is:
(a) $(C_1-C_8)$-alkyl,
(b) $(C_1-C_8)$-polyfluoroalkyl,
(c) 1-adamantyl,
(d) 1-naphthyl,
(e) (1-naphthyl)ethyl, or
(f) —$(CH_2)_p$-phenyl;

R$^6$ is:
(a) H,
(b) $(C_1-C_6)$-alkyl,
(c) $(C_3-C_6)$-cycloalkyl,
(d) phenyl, or
(e) benzyl;

R$^7$ is:
(a) H,
(b) $(C_1-C_8)$-alkyl,
(c) $(C_1-C_8)$-polyfluoroalkyl,
(d) $(C_3-C_6)$-cycloalkyl,
(e) phenyl,
(f) benzyl;

R$^8$ is:
(a) H,
(b) $(C_1-C_6)$-alkyl,
(c) $(C_3-C_6)$-cycloalkyl,
(d) —$(CH_2)_p$-phenyl,
(e) —OR$^6$,
(F) morpholin-4-yl, or
(g) —NR$^{15}$R$^{16}$;

R$^9$ and R$^{10}$ are each independently;
(a) H,
(b) Cl, Br, I, F,
(c) NO$_2$,
(d) $(C_1-C_6)$-alkyl,
(e) $((C_1-C_6)$-acyloxy,
(f) $(C_3-C_6)$-cycloalkyl,
(g) $(C_6-C_6)$-alkoxy,
(h) —NHSO$_2$R$^{2a}$,
(i) hydroxy-$(C_1-C_4)$-alkyl,
(j) $(C_1-C_4)$-alkyl-aryl,
(k) S(O)$_n$-$(C_1-C_4)$-alkyl,
(l) NR$^{2a}$R$^{2a}$,
(m) CF$_3$,
(n) —SO$_2$NHR$^{2a}$,
(o) furyl,
(p) aryl, or
(q) when R$^9$ and R$^{10}$ are bonded to adjacent carbon atoms, they can be joined to form a phenyl or naphthyl ring;

—X$^1$—X$^2$—X$^3$—X$^4$— is:
(a) -CR$^{11}$-Y-CR$^{12}$-CZ-,
(b) -CR$^{11}$-CR$^{12}$-Y-CZ-,
(c) -Y-CR$^{11}$-CZ-CR$^{12}$-,
(d) -CR$^{11}$-Y-CZ-CR$^{12}$-, or
(e) -CR$^{11}$-CR$^{12}$-CZ-Y-;

Y is: O, S, SO, or SO$_2$;

R$^{11}$ and R$^{12}$ are independently:
(a) H,
(b) Cl, Br, I, F,
(c) NO$_2$,
(d) NH$_2$,
(e) NH[$(C_1-C_4)$-alkyl],
(f) N[$(C_1-C_4)$-alkyl]$_2$,
(g) SO$_2$NHR$^{2a}$,
(h) CF$_3$,
(i) $(C_1-C_7)$-alkyl,
(j) $(C_3-C_7)$-cycloalkyl,
(k) $(C_3-C_7)$-cycloalkyl,
(l) when R$^{11}$ and R$^{12}$ are bonded to adjacent carbon atoms, they can be joined to form a phenyl or naphthyl ring,
(m) O(CH$_2$)$_{n+1}$O(CH$_2$)$_s$CH$_3$,
(n) (CH$_2$)$_{n+1}$O(CH$_2$)$_s$CH$_3$,
(o) (CH$_2$)N(R$^{2a}$)$_2$,
(p) (CH$_2$)$_n$N[CH$_2$CH$_2$]$_2$O,
(q) (CH$_2$)$_n$N[CH$_2$CH$_2$]$_2$CH$_2$,
(r) CH(OR$^{2a}$)[$(C_1-C_7)$-alkyl],
(s) CHO,
(t) CO$_2$R$^{2a}$,
(u) CH=CH-R$^{2a}$,
(t) CH$_2$CR$^{2a}$=C(R$^{2a}$)$_2$,
(v) (CH$_2$)$_n$NCOR$^{2a}$,
(w) $(C_1-C_4)$-alkyl-aryl, or
(x) CH(R$^{2a}$)$_2$;

Z is:
(a) -SO$_3$R$^{13}$,
(b) -NHSO$_2$CF$_3$,
(c) -PO(OR$^{13}$)$_2$,
(d) -SO$_2$NHR$^{2a}$,
(e) -CONHOR$^{13}$, (f) 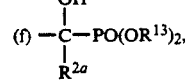—C—PO(OR$^{13}$)$_2$, with OH and R$^{2a}$ (g) -CN,
(h) -SO$_2$NH-CO-R$^{14}$,
(i) -CH$_2$SO$_2$NH-CO-R$^{14}$,
(j) -CONH-SO$_2$R$^{14}$,
(k) -CH$_2$CONH-SO$_2$R$^{14}$,
(l) -NHSO$_2$NHCO-R$^{14}$, or
(m) -NHCONHSO$_2$-R$^{14}$;

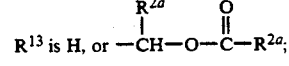
R$^{13}$ is H, or —CH—O—C—R$^{2a}$; with R$^{2a}$ and =O

R$^{14}$ is
(a) aryl,
(b) $(C_3-C_7)$-cycloalkyl, (c) ($C_1$-$C_4$)-alkyl, unsubstituted or substituted with a substituent selected from the group consisting of: aryl, -OH, -SH, ($C_1$-$C_4$)-alkyl, -($C_1$-$C_4$)-alkoxy, -S($C_1$-$C_4$)-alkyl, -$CF_3$, Cl, Br, F, I, -$NO_2$, -$CO_2H$, $CO_2$-($C_1$-$C_4$)-alkyl, -$NH_2$, -N[($C_1$-$C_4$)-alkyl]$_2$, -$PO_3H$ or PO(OH)(O-($C_1$-$C_4$)-alkyl),
(d) ($C_1$-$C_7$)-alkoxy,
(e) O($CH_2$)$_{n+1}$O($CH_2$)$_s$$CH_3$,
(f) ($CH_2$)$_{n+1}$O($CH_2$)$_s$$CH_3$,
(g) CH($R^{2a}$)$_2$,
(h) ($C_1$-$C_6$)-polyfluoroalkyl, or
(i) -NH-($C_1$-$C_6$)-alkyl;

$R^{15}$ and $R^{16}$ are independently:
(a) H,
(b) ($C_1$-$C_4$)-alkyl,
(c) phenyl,
(d) benzyl, or
(e) α-methylbenzyl;

$R^{19}$ is:
(a) H,
(b) ($C_1$-$C_6$)-alkyl,
(c) ($C_2$-$C_4$)-alkenyl,
(d) ($C_1$-$C_4$)-alkoxy, or
(e) benzyl, wherein the phenyl is unsubstituted or substituted with a substituent selected from the group consisting of: -$NO_2$, -$NH_2$, -OH or -$OCH_3$; and $R^{20}$ is -CN, -$NO_2$, -$CO_2R^{2a}$, or -$CF_3$.

2. The compound of claim 1 or its pharmceutically acceptable salt wherein:
$R^1$ is:
(a) ($C_1$-$C_6$)-alkyl, ($C_2$-$C_6$)-alkenyl or ($C_2$-$C_6$)-alkynyl each of which is unsubstituted or substituted with a substituent selected from the group consisting of:
  i) aryl, wherein aryl is defined as phenyl or naphthyl, unsubstituted or substituted with 1 or 2 substituents selected from the group consisting of:
    i) Br, I, Cl, F,
    ii) ($C_1$-$C_4$)-alkyl,
    iii) ($C_1$-$C_4$)-alkoxy,
    iv) ($C_3$-$C_7$)-cycloalkyl,
    v) ($C_3$-$C_{10}$)-alkenyl,
    vi) ($C_1$-$C_4$)-alkylthio,
    vii) OH,
    viii) $CO_2H$,
    ix) $CO_2$-($C_1$-$C_4$)-alkyl,
    x) $NO_2$,
    xi) $CF_3$,
    xii) $NH_2$,
    xiii) NH[($C_1$-$C_4$)-alkyl],
    xiv) N[($C_1$-$C_4$)-alkyl]$_2$,
    xv) $SO_2NR^{2a}R^{2a}$,
  ii) ($C_3$-$C_7$)-cycloalkyl,
  iii) Cl, Br, F,
  iv) OH,
  v) $NH_2$,
  vi) NH($C_1$-$C_4$)-alkyl,
  vii) N[($C_1$-$C_4$)-alkyl]$_2$,
  viii) $NHSO_2R^2$,
  ix) $CF_3$,
  x) $COOR^2$, or
  xi) $SO_2NHR^{2a}$, or
(b) ($C_1$-$C_4$)-polyfluoroalkyl;

E is a single bond, or —S—;

$R^2$ is:
(a) H, or
(b) ($C_1$-$C_6$)-alkyl;

$R^{2a}$ is:
(a) $R^2$,
(b) $CH_2$-aryl, or
(c) aryl;

n is 0 to 2;
s is 0 to 5;
m is 1 to 5;
p is 0 to 3;
x is 1 to 10;

$R^3$ is:
(a) H,
(b) ($C_1$-$C_6$)-alkyl, ($C_2$-$C_6$)-alkenyl or ($C_2$-$C_6$)-alkynyl,
(c) Cl, Br, I, F,
(d) $NO_2$
(e) $CF_3$,
(f) ($C_1$-$C_8$)-polyfluoroalkyl,
(g) $C_6F_5$,
(h) CN,
(i) phenyl,
(j) phenyl-($C_1$-$C_3$)-alkyl,
(k) phenyl and phenyl-($C_1$-$C_3$)-alkyl substituted on the phenyl ring with one or two substituents selected from:
  i) ($C_1$-$C_4$)-alkyl,
  ii) ($C_1$-$C_4$)-alkoxyl,
  iii) F, Cl, Br, I,
  iv) hydroxyl,
  v) methoxyl,
  vi) $CF_3$,
  vii) $CO_2R^{2a}$,
  viii) $NO_2$, or
  ix) $SO_2NR^{2a}R^{2a}$;

$R^4$ is:
(a) H,
(b) CN,
(c) ($C_1$-$C_8$)-alkyl,
(d) ($C_3$-$C_6$)-alkenyl,
(e) ($C_1$-$C_8$)-polyfluoroalkyl,
(f) ($C_1$-$C_8$)-polyfluoroalkenyl,
(g) $CF_2CF_3$,
(h) $CO_2R^{2a}$,
(i) phenyl,
(j) phenyl-($C_2$-$C_6$)-alkenyl,

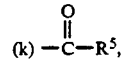
(k) —C—$R^5$,

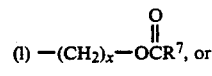
(l) —($CH_2$)$_x$—$OCR^7$, or

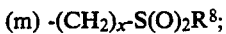
(m) -($CH_2$)$_x$-S(O)$_2R^8$;

$R^7$ is:
(a) H,
(b) ($C_1$-$C_8$)-alkyl,
(c) ($C_1$-$C_8$)-polyfluoroalkyl,
(d) ($C_3$-$C_6$)-cycloalkyl,
(e) phenyl, or
(f) benzyl;

$R^8$ is:
(a) H,
(b) $C_1$-$C_6$)-alkyl,
(c) ($C_3$-$C_6$)-cycloalkyl,
(d) -($CH_2$)$_p$-phenyl,
(e) -$OR^6$,
(f) morpholin-4-yl, or (g) -NR$^{15}$R$^{16}$;

R$^9$ and R$^{10}$ are each independently;
(a) H,
(b) Cl, Br, I, F, (c) NO$_2$,
(d) C$_1$-C$_6$-alkyl,
(e) C$_1$-C$_6$-acyloxy,
(f) (C$_3$-C$_6$)-cycloalkyl,
(g) C$_1$-C$_6$-alkoxy,
(h) -NHSO$_2$R$^{2a}$,
(i) hydroxy-(C$_1$-C$_4$)-alkyl,
(j) (C$_1$-C$_4$)-alkyl-aryl,
(k) S(O)$_n$-(C$_1$-C$_4$)-alkyl,
(l) NR$^{2a}$R$^{2a}$,
(m) CF$_3$,
(n) -SO$_2$NHR$^{2a}$,
(o) furyl,
(p) aryl, or
(q) when R$^9$ and R$^{10}$ are bonded to adjacent carbon atoms, they can be joined to form a phenyl or naphthyl ring;

—X$^1$—X$^2$—X$^4$— is:
(a) -CR$^{11}$-Y-CR$^{12}$-CZ-,
(b) -CR$^{11}$-CR$^{12}$-Y-CZ-,
(c) -Y-CR$^{11}$-CZ-CR$^{12}$-,
(d) -CR$^{11}$-Y-CZ-CR$^{12}$-, or
(e) -CR$^{11}$-CR$^{12}$-CZ-Y-;

Y is: O, S, SO, or SO$_2$;
Z is:
(a) -NHSO$_2$CF$_3$,
(b) -SO$_2$NHR$^{2a}$,
(c) -CN,
(d) -SO$_2$NHCOR$^{14}$,

R$^{11}$ and R$^{12}$ are independently:
(a) H,
(b) Cl, Br, I, F,
(c) NO$_2$,
(d) NH$_2$,
(e) NH[(C$_1$-C$_4$)-alkyl],
(f) N[(C$_1$-C$_4$)-alkyl]$_2$,
(g) SO$_2$NHR$^{2a}$,
(h) CF$_3$,
(i) ($_1$-C$_7$)-alkyl,
(j) C$_1$-C$_6$-alkoxy,
(k) (C$_3$-C$_7$)-cycloalkyl,
(l) when R$^{11}$ and R$^{12}$ are bonded to adjacent carbon atoms, they can be joined to form a phenyl or naphthyl ring,
(m) O(CH$_2$)$_{n+1}$O(CH$_2$)$_s$CH$_3$,
(n) (CH$_2$)$_{n+1}$O(CH$_2$)$_s$CH$_3$,
(o) (CH$_2$)N(R$^{2a}$)$_2$,
(p) (CH$_2$)$_n$N[CH$_2$CH$_2$]$_2$O,
(q) (CH$_2$)$_n$N[CH$_2$CH$_2$]$_2$CH$_2$,
(r) CH(OR$^{2a}$)[(C$_1$-C$_7$)-alkyl],
(s) CHO,
(t) CO$_2$R$^{2a}$,
(u) CH=CH-R$^{2a}$,
(v) CH$_2$CR$^{2a}$=C(R$^{2a}$)$_2$,
(w) (CH$_2$)$_n$NCOR$^{2a}$,
(x) (C$_1$-C$_4$)-alkyl-aryl, or
(y) CH(R$^{2a}$)$_2$;

R$^{13}$ is H, or $-\text{CH}(R^{2a})-O-\overset{O}{\underset{\|}{C}}-R^{2a}$;

R$^{14}$ is
(a) aryl,
(b) (C$_3$-C$_7$)-cycloalkyl,
(c) (C$_1$-C$_4$)-alkyl, unsubstituted or substituted with a substituent selected from the group consisting of: aryl, —OH, —SH, (C$_1$-C$_4$)-alkyl, -(C$_1$-C$_4$)-alkoxy, -S((C$_1$-C$_4$)-alkyl, -CF$_3$, Cl, Br, F, I, -NO$_2$, -CO$_2$H, CO$_2$-(C$_1$-C$_4$)-alkyl, -NH$_2$, -N[(C$_1$-C$_4$)-alkyl]$_2$, -PO$_3$H or PO(OH)(O-(C$_1$-C$_4$)-alkyl),
(d) (C$_1$-C$_7$)-alkoxy,
(e) O(CH$_2$)$_{n+1}$O(CH$_2$)$_s$CH$_3$,
(f) (CH$_2$)$_{n+1}$O(CH$_2$)$_s$CH$_3$,
(g) CH(R$^{3a}$)$_2$,
(h) (C$_1$-C$_6$)-polyfluoroalkyl, or
(i) -NH-C$_1$-C$_6$-alkyl; and R$^{15}$ and R$^{16}$ are independently:
(a) H,
(b) (C$_1$-C$_4$)-alkyl,
(c) phenyl,
(d) benzyl,
(e) α-methylbenzyl.

3. A compound of structural formula I is or its pharmaceutically acceptable salt wherein:
R$^1$ is C$_1$-C$_6$-alkyl, (C$_3$-C$_8$)-cycloalkyl, or (C$_1$-C$_4$)-alkyl-(C$_3$-C$_8$)-cycloalkyl;
n is: 0, 1 or 2;
s is: 0 to 5;
R$^2$ is: H or C$_1$-C$_6$-alkyl;
R$^3$ is H, Cl, (C$_1$-C$_4$)-polyfluoroalkyl, (C$_1$-C$_4$)-alkylamino, (C$_1$-C$_4$)-acylamino;
R$^4$ is CO$_2$H, CH$_2$OH, or CO$_2$(C$_1$-C$_4$)-alkyl;
—X$^1$—X$^2$—X$^3$—X$^4$— is:
(a) -CR$^{11}$-Y-CR$^{12}$-CZ-, or
(b) -CR$^{11}$-CR$^{12}$-Y-CZ-;

R$^{11}$ and R$^{12}$ are independently:
H, C$_1$-C$_6$-alkyl, C$_1$-C$_6$-alkoxy, (C$_1$-C$_4$)-alkyl-aryl, O(CH$_2$)$_{n+1}$O(CH$_2$)$_s$CH$_3$, (CH$_2$)$_{n+1}$O(CH$_2$)$_s$CH$_3$, (CH$_2$)$_n$N[CH$_2$CH$_2$]$_2$O or when R$^{11}$ and R$^{12}$ are bonded to adjacent carbon atoms, they can joined to form an phenyl ring;

Y is: O, or S;
Z is:
(a) CONHSO$_2$R$^{14}$,
(b) SO$_2$NHR$^{14}$,
(c) NHSO$_2$R$^{14}$,
(d) SO$_2$NHCOR$^{14}$, or
(e) NHSO$_2$CF$_3$; and R$^{14}$ is:
(a) C$_1$-C$_6$-alkyl,
(b) C$_1$-C$_6$-alkoxy,
(c) phenyl,
(d) CH$_2$-phenyl, (e) CH(phenyl)$_2$,
(f) (C$_3$-C$_6$)-cycloalkyl,
(g) (C$_1$-c$_3$)-alkyl-(C$_3$-C$_6$)-cycloalkyl,
(h) (CH$_2$)$_5$NH$_2$,
(i) O(CH$_2$)$_{n+1}$O(CH$_2$)$_s$CH$_3$,
(j) (CH$_2$)$_{n+1}$O(CH$_2$)$_s$CH$_3$,
(k) (C$_1$-C$_4$)-polyfluoroalkyl, or
(l) NH-(C$_1$-C$_4$)-alkyl.

4. A compound in which the structural formula Ia is

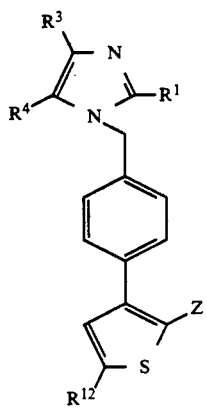

Ia or its pharmaceutically acceptable salt wherein:
R$^1$ is: ethyl, n-propyl, n-butyl, or cyclopropyl;
n is: 0, 1 or 2;
s is: 0 to 5;
R$^2$ is: H or C$_1$-C$_6$-alkyl;
R$^3$ is H, Cl, (C$_1$-C$_4$)-polyfluoroalkyl, (C$_1$-C$_4$)-alkylamino, (C$_1$-C$_4$)-acylamino;
R$^4$ is CO$_2$H, CH$_2$OH, or CO$_2$(C$_1$-C$_4$)-alkyl;
R$^{12}$ is: H, C$_1$-C$_6$-alkyl, C$_1$-C$_6$-alkoxy, -CH$_2$-phenyl, O(CH$_2$)$_{n+1}$O(CH$_2$)$_s$CH$_3$, (CH$_2$)$_{n+1}$O(CH$_2$)$_s$CH$_3$, or CH$_2$N[CH$_2$CH$_2$]$_2$O;

Z is:
(a) CO$_2$R$^2$,
(b) CONHSO$_2$R$^{14}$,
(c) SO$_2$NHR$^{14}$,
(d) NHSO$_2$R$^{14}$,
(e) SO$_2$NHCOR$^{14}$, or
(f) NHSO$_2$CF$_3$; and
R$^{14}$ is:
(a) C$_1$-C$_6$-alkyl,
(b) C$_1$-C$_6$-alkoxy,
(c) phenyl,
(d) CH$_2$-phenyl,
(e) CH(phenyl)$_2$,
(f) (C$_3$-C$_6$)-cycloalkyl,
(g) (C$_1$-C$_3$)-alkyl-(C$_3$-C$_6$)-cycloalkyl,
(h) (CH$_2$)$_5$NH$_2$,
(i) O(CH$_2$)$_{n+1}$O(CH$_2$)$_s$CH$_3$,
(j) (CH$_2$)$_{n+1}$O(CH$_2$)$_s$CH$_3$,
(k) (C$_1$-C$_4$)-polyfluoroalkyl, or
(l) NH-(C$_1$-C$_4$)-alkyl.

5. A compound of structural formula I:

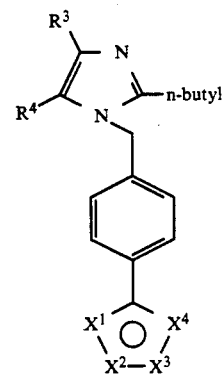

I wherein the compound is selected from the table below:

| R$^3$ | R$^4$ | —X$^1$—X$^2$—X$^3$—X$^4$— | R$^{12}$ | Z |
|---|---|---|---|---|
| Cl | CH$_2$OH | —C—C—S—CZ— (with HC-O-CH, HC—CH ring) | | SO$_2$NHCOPh |
| Cl | CO$_2$H | —C—C—S—CZ— (with HC-O-CH, HC—CH ring) | | SO$_2$NHCOPh |
| Cl | CH$_2$OH | —CH—CH—S—CZ— | | SO$_2$NHCOPh |
| Cl | CO$_2$H | —CH—CH—S—CZ— | | SO$_2$NHCOPh |
| NO$_2$ | CO$_2$H | —CH—CH—S—CZ— | | SO$_2$NHCOPh |
| CF$_3$ | CO$_2$H | —CH—CH—S—CZ— | | SO$_2$NHCOPh |
| Cl | CH$_2$OH | —CH—CR$^{12}$—S—CZ— | Me | SO$_2$NHCOPh |
| Cl | CH$_2$OH | —CH—CR$^{12}$—S—CZ— | Et | SO$_2$NHCOPh |
| Cl | CH$_2$OH | —CH—CR$^{12}$—S—CZ— | nPr | SO$_2$NHCOPh |
| Cl | CH$_2$OH | —CH—CR$^{12}$—S—CZ— | nBu | SO$_2$NHCOPh |
| Cl | CH$_2$OH | —CH—CR$^{12}$—S—CZ— | iBu | SO$_2$NHCOPh |
| Cl | CH$_2$OH | —CH—CR$^{12}$—S—CZ— | nPn | SO$_2$NHCOPh |
| Cl | CH$_2$OH | —CH—CR$^{12}$—S—CZ— | Bn | SO$_2$NHCOPh |
| Cl | CH$_2$OH | —CH—CR$^{12}$—S—CZ— | CH$_2$N(CH$_2$CH$_2$)$_2$O | SO$_2$NHCOPh |
| Cl | CH$_2$OH | —CH—CR$^{12}$—S—CZ— | CH$_2$N(CH$_2$CH$_2$)$_2$O | SO$_2$NHCOCH(Ph)$_2$ |
| Cl | CH$_2$OH | —CH—CR$^{12}$—S—CZ— | nPr | SO$_2$NHCO(CH$_2$)$_2$OMe |
| Cl | CH$_2$OH | —CH—CR$^{12}$—S—CZ— | Me | SO$_2$NHCOCH$_2$Ph |
| Cl | CH$_2$OH | —CH—CR$^{12}$—S—CZ— | Me | SO$_2$NHCOCH(Ph)$_2$ |
| Cl | CH$_2$OH | —CH—CR$^{12}$—S—CZ— | Et | SO$_2$NHCOCH(Ph)$_2$ |
| Cl | CH$_2$OH | —CH—CR$^{12}$—S—CZ— | Et | SO$_2$NHCOCH$_2$OEt |
| Cl | CH$_2$OH | —CH—CR$^{12}$—S—CZ— | nBu | SO$_2$NHCOCH$_2$OEt |
| Cl | CH$_2$OH | —CH—CR$^{12}$—S—CZ— | nPr | SO$_2$NHCOCH$_2$OBu |

-continued

| R³ | R⁴ | —X¹—X²—X³—X⁴— | R¹² | Z |
|---|---|---|---|---|
| Cl | CH₂OH | —CH—CR¹²—S—CZ— | nBu | SO₂NHCO(CH₂)₂cyclopentyl |
| Cl | CH₂OH | —CH—CR¹²—S—CZ— | iBu | SO₂NHCOCH₂OBu |
| Cl | CH₂OH | —CH—CR¹²—S—CZ— | iBu | SO₂NHCOCH₂OEt |
| Cl | CH₂OH | —CH—CR¹²—S—CZ— | nPn | SO₂NHCOCH₂OEt |
| Cl | CH₂OH | —CH—CR¹²—S—CZ— | nPn | SO₂NHCOCH₂OBu |
| Cl | CH₂OH | —CH—CR¹²—S—CZ— | nPr | SO₂NHCOOCH₂CH(Me)₂ |
| Cl | CH₂OH | —CH—CR¹²—S—CZ— | iBu | SO₂NHCOO(CH₂)₂OMe |
| Cl | CH₂OH | —CH—CR¹²—S—CZ— | nBu | SO₂NHCO(CH₂)₅NHCO₂-t-butyl |
| Cl | CH₂OH | —CH—CR¹²—S—CZ— | nBu | SO₂NHCO(CH₂)₅NH₂ |
| Cl | CH₂OH | —CH—CR¹²—S—CZ— | iBu | SO₂NHCO(CH₂)₅NHCO₂-t-butyl |
| Cl | CH₂OH | —CH—CR¹²—S—CZ— | iBu | SO₂NHCO(CH₂)₅NH₂ |
| Cl | CH₂OH | —CH—CR¹²—S—CZ— | nPn | SO₂NHCO(CH₂)₅NHCO₂-t-butyl |
| Cl | CH₂OH | —CH—CR¹²—S—CZ— | nPn | SO₂NHCO(CH₂)₅NH₂ |
| Cl | CH₂OH | —CH—CR¹²—S—CZ— | nPr | SO₂NHCO(CH₂)₄CH₃ |
| Cl | CH₂OH | —CH—CR¹²—S—CZ— | Bn | SO₂NHCOcyclopropyl |
| Cl | CH₂OH | —CH—CR¹²—S—CZ— | nPr | SO₂NHCOOBu |
| Cl | CH₂OH | —CH—CR¹²—S—CZ— | nBu | SO₂NHCOOBu |
| Cl | CH₂OH | —CH—CR¹²—S—CZ— | iBu | SO₂NHCOOBu |
| Cl | CH₂OH | —CH—CR¹²—S—CZ— | nPn | SO₂NHCOOBu |
| Cl | CH₂OH | —CH—CR¹²—S—CZ— | nPr | SO₂NHCOCH(Ph)₂ |
| Cl | CH₂OH | —CH—CR¹²—S—CZ— | nPr | SO₂NHCOCH₂OEt. |

6. A pharmaceutical composition useful in the treatment of hypertension which comprises a pharmaceutically acceptable carrier and a therapeutically effective amount of a compound of claim 1.

7. An ophthalmological formulation for the treatment of ocular hypertension comprising an ophthalmologically acceptable carrier and an effective ocular antihypertensive amount of a compound of claim 1.

8. A method of treating hypertension which comprises administering to a patient in need of such treatment a therapeutically effective amount of a compound of claim 1.

9. A method of treating ocular hypertension comprising topical ocular administration to a patient in need of such treatment of an effective ocular antihypertensive amount of a compound of claim 1.

* * * * *